US008613720B2

(12) United States Patent
Bendek et al.

(10) Patent No.: US 8,613,720 B2
(45) Date of Patent: *Dec. 24, 2013

(54) AUTOMATIC RECONSTITUTION INJECTOR DEVICE

(75) Inventors: Antonio Bendek, Vernon, NJ (US); John Laiosa, Lodi, NJ (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/314,292

(22) Filed: Dec. 8, 2011
(Under 37 CFR 1.47)

(65) Prior Publication Data

US 2012/0078172 A1 Mar. 29, 2012

Related U.S. Application Data

(63) Continuation of application No. 11/791,600, filed as application No. PCT/US2005/042426 on Nov. 22, 2005, now Pat. No. 8,092,420.

(60) Provisional application No. 60/630,947, filed on Nov. 24, 2004.

(51) Int. Cl.
*A61M 37/00* (2006.01)
*A61M 5/00* (2006.01)

(52) U.S. Cl.
USPC ............... 604/89; 604/91; 604/92; 604/207; 604/208; 604/218; 604/232; 604/246

(58) Field of Classification Search
USPC ............... 604/135, 207–211, 218, 232, 234, 604/89–92
See application file for complete search history.

(56) References Cited

U.S. PATENT DOCUMENTS

| | | | |
|---|---|---|---|
| 4,968,299 A | 11/1990 | Ahlstrand et al. | |
| 5,980,491 A | 11/1999 | Hansen | |
| 6,221,046 B1 | 4/2001 | Burroughs et al. | |
| 6,793,646 B1* | 9/2004 | Giambattista et al. | 604/90 |
| 2001/0009990 A1 | 7/2001 | Hostettler et al. | |
| 2004/0133163 A1* | 7/2004 | Schiffmann | 604/131 |

FOREIGN PATENT DOCUMENTS

| | | |
|---|---|---|
| EP | 0 405 320 A2 | 1/1991 |
| EP | 0 943 349 A1 | 9/1999 |

OTHER PUBLICATIONS

PCT International Search Report, PCT/US2005/042426, dated Jun. 29, 2006, 4 pages.

* cited by examiner

*Primary Examiner* — Nicholas Lucchesi
*Assistant Examiner* — Leah Stohr
(74) *Attorney, Agent, or Firm* — Hoffmann & Baron, LLP

(57) ABSTRACT

The present invention is directed to an automatic reconstitution drug delivery device. The inventive device effects simple and automatic reconstitution of a dry drug. To effect reconstitution, a user displaces a release button which causes first and second chambers of a drug cartridge to communicate, resulting in automatic mixing of a diluent and dry drug to effect reconstitution of the dry drug. The user then simply sets the dose volume using a dose-setting mechanism, and administers the injection in a manner typical of self-injection drug delivery devices. Whole or partial automatic priming can be also achieved by the device.

26 Claims, 20 Drawing Sheets

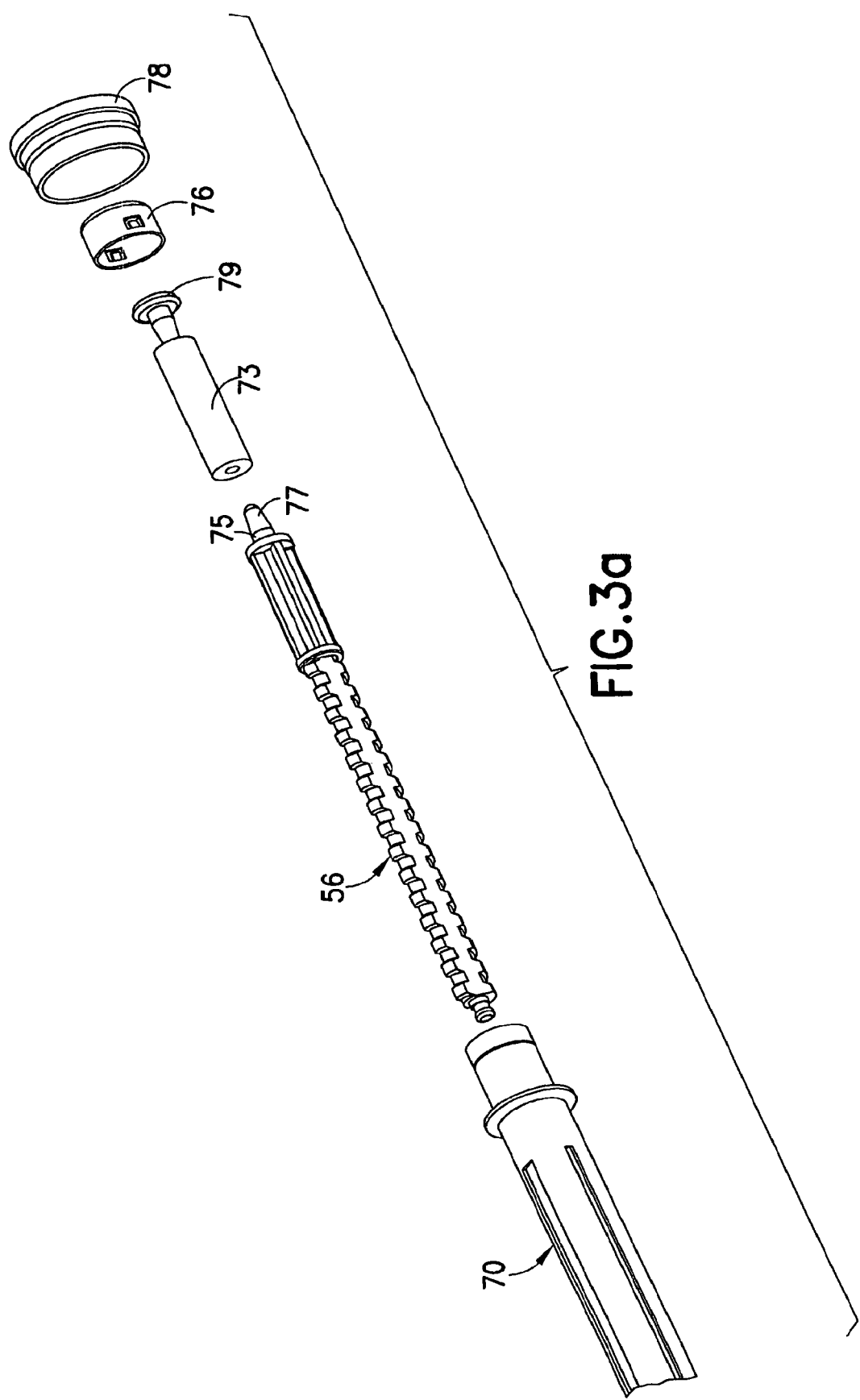

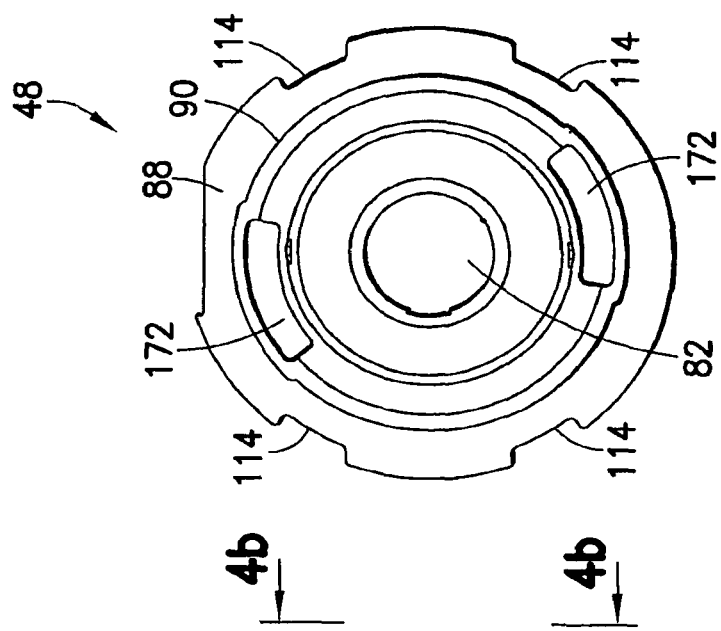
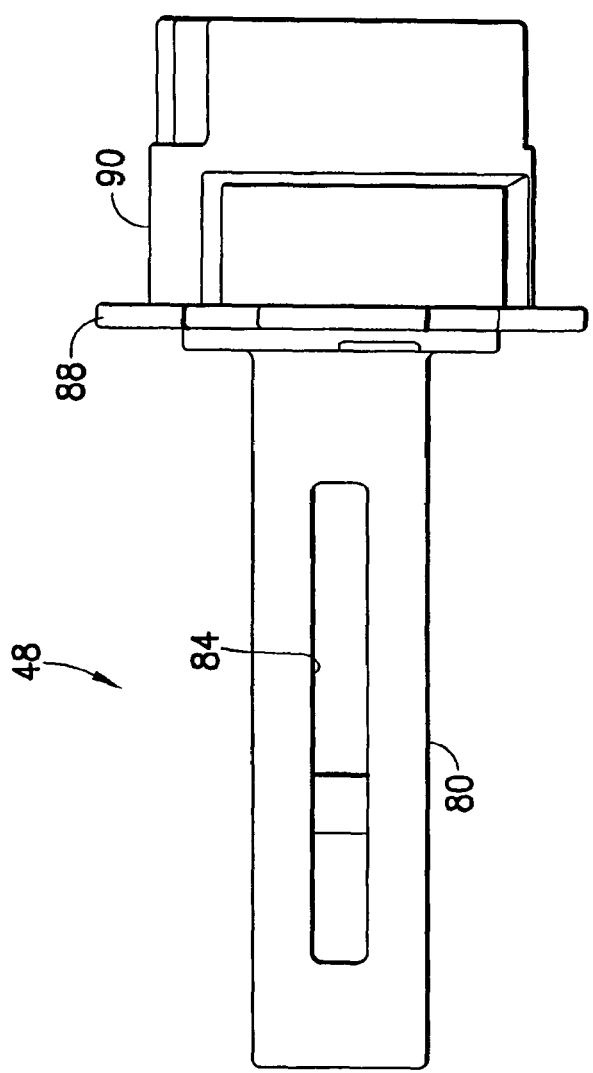
FIG.4b
FIG.4a

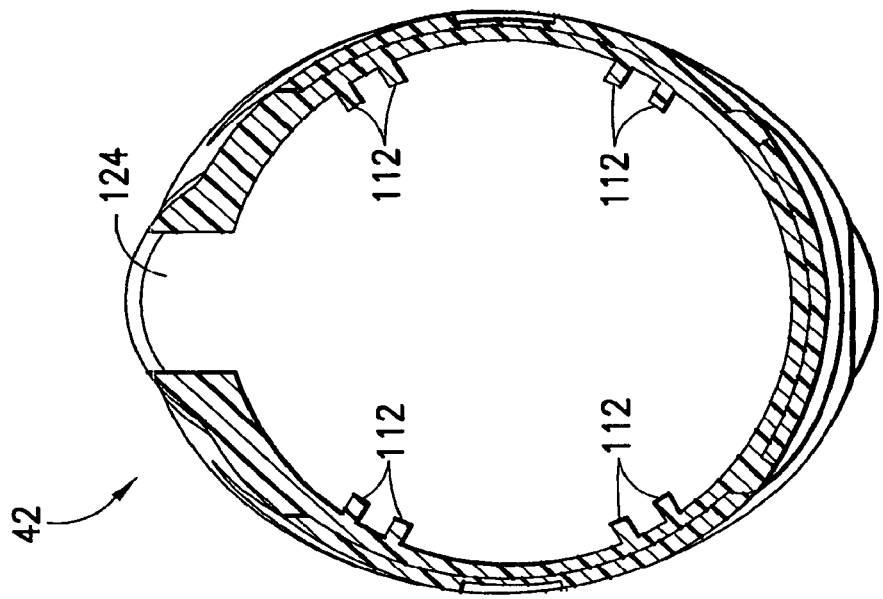
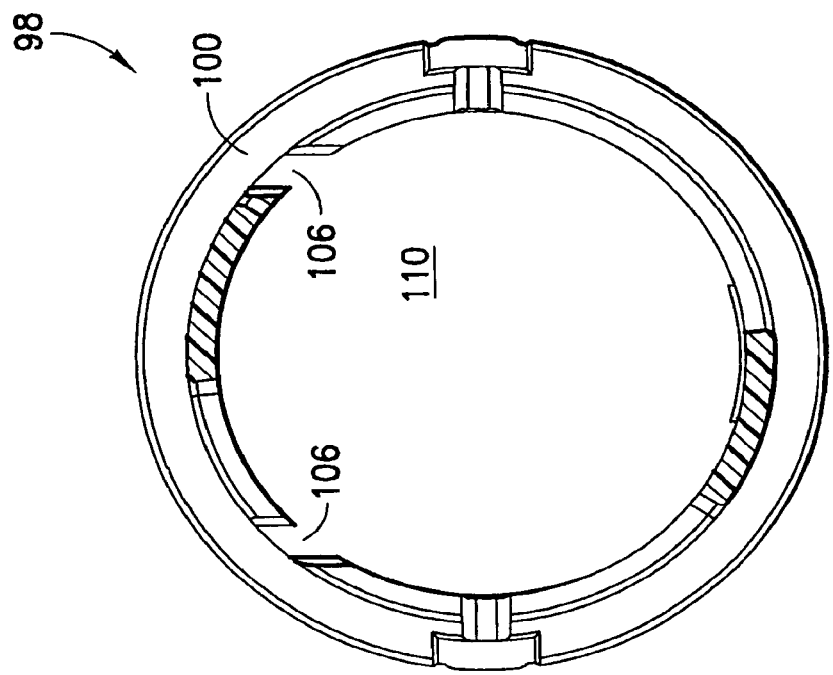

AUTOMATIC RECONSTITUTION INJECTOR DEVICE

CROSS-REFERENCES TO RELATED APPLICATIONS

This application is a continuation of U.S. application Ser. No. 11/791,600, filed May 24, 2007, now allowed, which is a National Stage Application under §371 of PCT Appl. No. PCT/US2005/042426, filed Nov. 22, 2005, which claims priority to U.S. Provisional Appl. No. 60/630,947, filed Nov. 24, 2004, the entireties of which are incorporated by reference herein.

FIELD OF THE INVENTION

This invention relates to self-injection drug delivery devices that automatically reconstitute a dry drug into liquid form.

BACKGROUND OF THE INVENTION

Medication delivery pens have been developed to facilitate the administration of medication, particularly the self-administration of medication. Such medication delivery pens may be referred to herein as an injector device, a self-injection drug delivery device, a pen style drug delivery device, a pen, and other variations thereof. Such pens may be disposable, containing a single dose of a drug, or reusable, containing a single dose or more of a drug. The pen typically includes a vial or drug cartridge containing a drug and a dose setting mechanism which allows both for selecting a dose of medication to be delivered by the pen and for urging a plunger of the vial in a distal direction for a distance corresponding to the selected dose, thereby allowing the dose to be administered.

Certain drugs or medicaments (those terms being used interchangeably herein) are preferably provided in powder or dry form (sometimes referred to a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other powder form that require reconstitution.

Prior art devices have been developed that provide the diluent and lyophilized substance in separate chambers of a common container. Such devices permit manual reconstitution of the drug prior to administration. U.S. Pat. No. 4,874,381 to Vetter and U.S. Pat. No. 4,968,299 to Ahlstrand et al. are examples of manually activated devices which require a user to physically move one or more components to perform a reconstitution process. U.S. Pat. No. 6,793,646 to Giambattista et al. shows a device which allows for automated reconstitution. Specifically, to activate the device and effect reconstitution of the dry drug, the user manually causes certain components to move relative to one another axially to obtain reconstitution of a medication. The device of U.S. Pat. No. 6,793,646, however, is a single dose device which is disposable, not reusable. In addition, the device has limited variation in deliverable dosage amounts, based on a fixed arrangement of parts.

Certain drugs, once reconstituted, may have a shelf-life of several days or months. For example, human growth hormone (HGH) may have a shelf-life of up to thirty (30) days once reconstituted. For such drugs, it may be desirable to have a device which enables the user to administer repeated dosing of varying volumes of reconstituted drugs or medicaments, thus allowing for multiple doses to be administered over time.

SUMMARY OF THE INVENTION

The present invention is directed to an automatic reconstitution drug delivery device. The inventive device effects simple and automatic reconstitution of a dry drug. To effect reconstitution, a user displaces a release button which causes first and second chambers of a drug cartridge to communicate, resulting in automatic mixing of a diluent and dry drug to effect reconstitution of the dry drug. The user then simply sets the dose volume using a dose-setting mechanism, and administers the injection in a manner typical of self-injection drug delivery devices. Whole or partial automatic priming can be also achieved by the device.

In a further aspect of the subject invention, an injector device for automatic reconstitution of a substance is provided herein having a dose-setting mechanism with a cartridge engagement surface extending therefrom. The dose-setting mechanism is adjustable to set a dose for the injector device. The injector device further includes a housing cooperatively engaging the dose-setting mechanism, and a biasing means for selectively moving the dose-setting mechanism from a first position to a second position relative to the housing. The cartridge engagement surface moves a predetermined distance relative to the housing with the dose-setting mechanism moving from the first position to the second position. Advantageously, the subject invention allows for the dose-setting mechanism to be moved relative to the housing to cause automatic reconstitution of a drug substance. The force of movement of the cartridge engagement surface is translated to a multi-chambered drug cartridge which, in turn, may utilize the force of movement to cause reconstitution of the contents of the drug cartridge using any known technique.

Various dose-setting mechanisms can be used with the subject invention. In addition, various features can be optionally used with the injector device, such as, a releasable attachment for the drug cartridge, and a releasable retainer for maintaining the dose-setting mechanism in the first position against the biasing means.

The injector device may also be included as part of a kit which further includes a mandrel for setting the dose-setting mechanism to the first position from the second position.

These and other features of the invention will be better understood through a study of the following detailed description and accompanying drawings.

BRIEF DESCRIPTION OF THE DRAWINGS

FIG. 3a is an enlarged view showing a resilient tube usable in the dose-setting mechanism;

FIG. 4a is a side elevational view of a body adapter;

FIG. 4b is an end view of the body adapter as viewed along line 4b-4b of FIG. 4a;

FIG. 5 is a cross-sectional view of a spring seat taken along line 5-5 of FIG. 2;

FIG. 6 is a cross-sectional view of a rear housing taken along line 6-6 of FIG. 2;

DETAILED DESCRIPTION OF THE INVENTION

Figure 1:
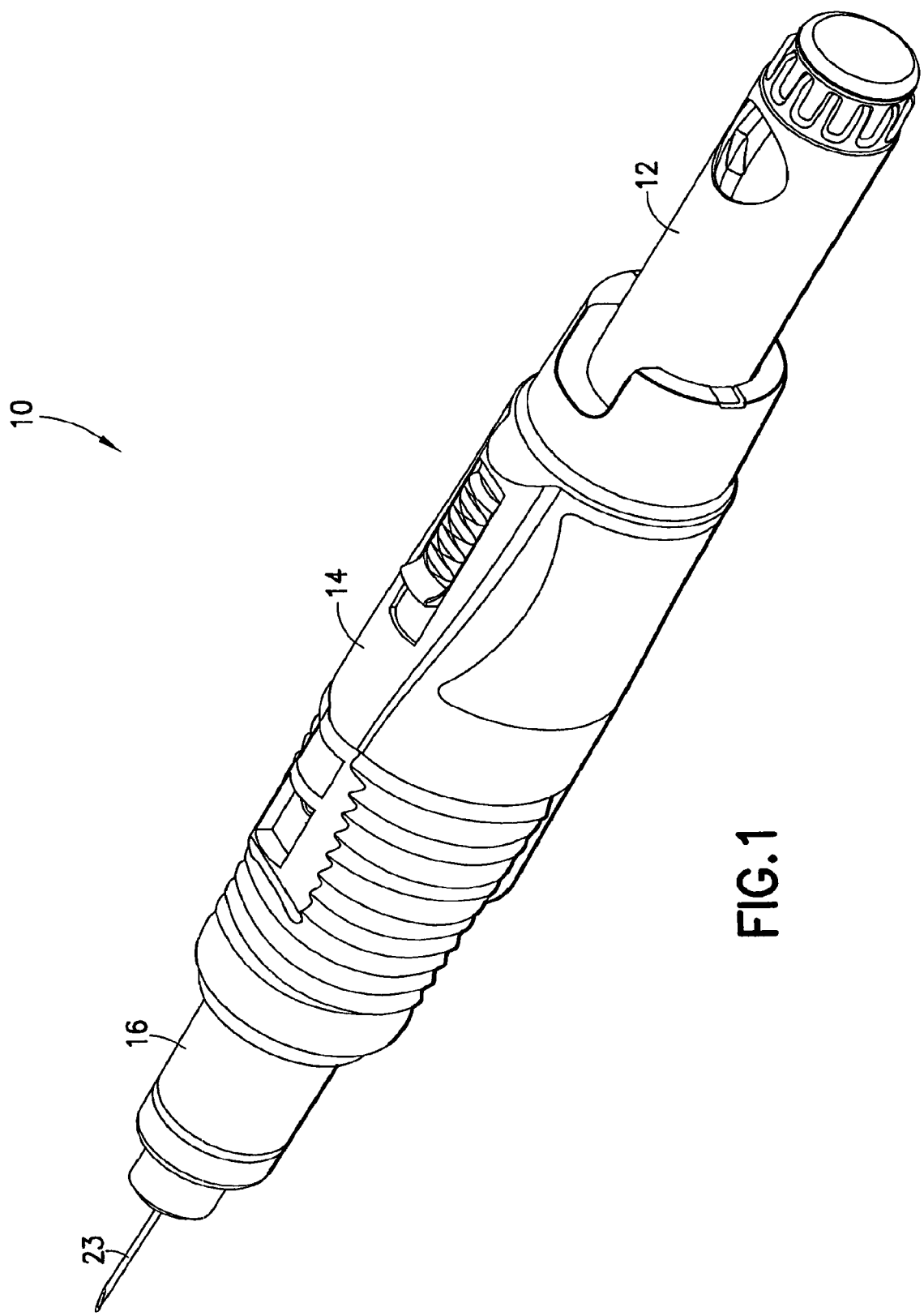
FIG. 1 is a perspective view of an automatic reconstitution injector device formed in accordance with the subject invention.

With reference to FIG. 1, an automatic reconstitution injector device 10 in accordance with an embodiment of the present invention is there depicted. The inventive injector device 10 may be used to administer one or more injections of a drug or a medicament. The injector device 10 generally includes a dose-setting mechanism 12, a housing 14, and a drug cartridge assembly 16.

As used herein, the term "proximal", and derivatives thereof, refer to a direction towards the rear of the injector body and away from a patient, while the term "distal", and derivatives thereof, refer to a direction towards the front of the injector device and closer to a patient.

The drug cartridge assembly 16 includes a drug cartridge or vial 216 that may be formed of any known material, such as glass or plastic. By way of non-limiting example, and with reference to FIGS. 10 and 11, the drug cartridge 216 includes a distal end 18 with an opening 20 formed therein sealed by a pierceable septum 22. As is known in the art, the septum 22 is pierceable by a needle cannula 23 and re-sealable upon removal of the needle cannula 23. Typically, the needle cannula 23 will be double-ended with both ends being sharpened, a proximal end 25 for piercing the septum 22 and a distal end 27 for insertion into a patient. The drug cartridge 216 further includes a proximal end 24 which is open and sealable by a first stopper 26 that is movably disposed in the drug cartridge 216 to slide along the length thereof and maintain a seal with the wall of the drug cartridge 216. The first stopper 26 is engageable by the dose-setting mechanism 12, directly or indirectly, to force movement thereof.

The drug cartridge 216 may be a multi-chambered cartridge including at least first and second chambers for containing a first and second liquid or dry substance. For example, a reconstitutable substance, e.g. a lyophilized substance, may be disposed in one chamber with a diluent suitable for reconstituting the reconstitutable substance being disposed in a separate, second chamber. Reconstitution is achieved with communication being allowed between the two chambers. Various configurations are known in the art to selectively permit communication. By way of non-limiting example, and again with reference to FIG. 10, a second stopper 28 may be disposed in the drug cartridge 216 spaced from the first stopper 26 in an initial state. Accordingly, a first chamber 30 is defined between the first and second stoppers 26, 28, and a second chamber 32 is defined between the second stopper 28 and the septum 22 at the distal end 18 of the drug cartridge 216. A dry, reconstitutable substance 34 may be disposed in the second chamber 32, while a diluent 36 suitable for reconstituting the reconstitutable substance 34 may be disposed in the first chamber 30. In the initial state, the second stopper 28 prevents communication between the first and second chambers 30, 32 during transportation and up to reconstitution, which, preferably occurs just before administration. With the exemplary configuration, to achieve reconstitution, the first stopper 26 is caused to be driven distally with the second stopper 28 moving in response to the force of movement of the first stopper 26. The force of movement may be translated to the second stopper 28 via the diluent 36 with the diluent 36 being generally incompressible. One or more communication channels 38 may be formed in the wall of the drug cartridge 216 adapted to by-pass the second stopper 28 over a range of movement of the second stopper 28. With the second stopper 28 moving a sufficient distance, the communication channel 38 establishes communication between the first and second chambers 30, 32. The communication channel 38 has sufficient length to permit communication between the first and second chambers 30, 32 about the second stopper 28. With the first and second chambers 30, 32 being in open communication, the diluent 36 is urged into the second chamber 32 with further distal movement of the first stopper 26. With continued movement, the first stopper 26 collapses the first chamber 30 and comes into contact with the second stopper 28 (FIG. 11). The reconstitution process is terminated with further movement of the second stopper 28, under force of movement of the first stopper 26, to a position where the second chamber 32, and reconstituted substance 37, is sealed from the communication channel 38. With the needle cannula 23 extending through the septum 22 into communication with the second chamber 32, additional movement of the first stopper 26 can urge the reconstituted substance 37 from the second chamber 32 and into the needle cannula 23 for administration.

As will be recognized by those skilled in the art, various drug cartridges and container designs exist which allow for selective communication between initially-separate chambers in permitting reconstitution of a drug or medicament. Alternative communication passages and arrangements can be utilized with the subject invention including specially designed stoppers or valve mechanisms, such as those shown in U.S. Pat. Nos. 5,713,857 and 4,929,230, the disclosures of which are both incorporated by reference herein. In addition, more than two chambers may be used as shown in U.S. Pat. No. 5,865,798 depending on the particular substance to be reconstituted. As will be further appreciated by those skilled in the art, any reconstitutable substance may be used with subject invention, such as a drug or medicament in powdered form which is not lyophilized.

The needle cannula 23 is preferably fixed relative to the housing 14. In particular, the needle cannula 23 is fixed to the housing 14 so that there is no relative movement therebetween during the reconstitution process or otherwise. The needle cannula 23 may be fixed using any known manner, such as being threadedly mounted or being rigidly staked to the drug cartridge assembly 16. Alternatively, or in addition to, the needle cannula 23 may be directly fixed to the housing 14. It may be desired to have the needle cannula 23 be removably fixed to allow for replacement and multiple uses with the same drug cartridge 216, or permanently fixed, such as where the injector device 10 is intended as a single-use device.

Figure 2:
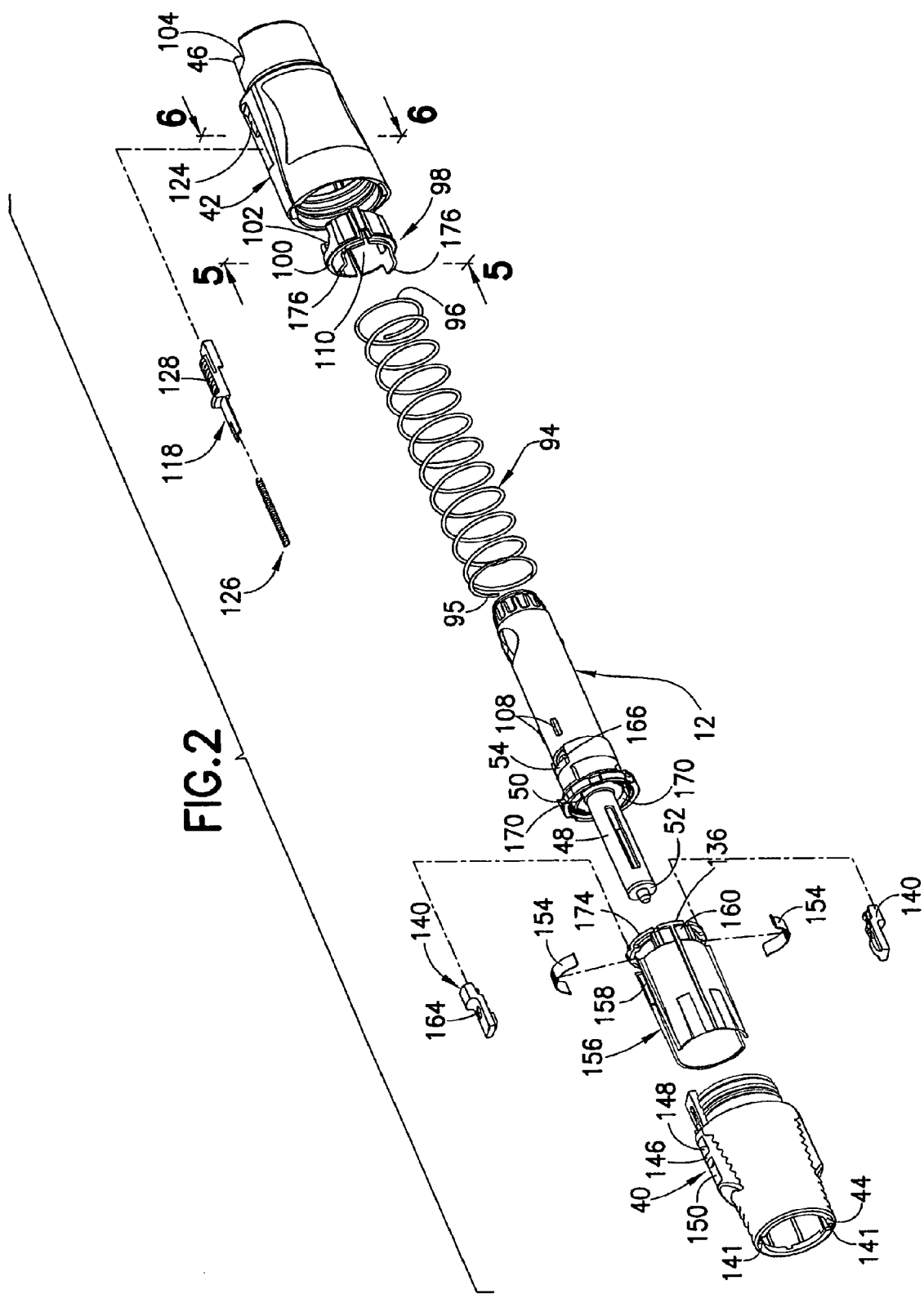
FIG. 2 is an exploded view of a portion of the injector device of the subject invention.

With reference to FIG. 2, the housing 14 may include a front housing 40 and a rear housing 42 which are joinable using any known technique, including, but not limited to, an interference fit, bonding, and/or mechanical interaction of locking members. The front housing 40 defines an open distal end 44 of the injector device 10, while the rear housing 42 defines an open proximal end 46 of the injector device 10. The housing 14 is formed to accommodate the dose-setting mechanism 12 with a portion of the dose-setting mechanism 12 being accessible through the proximal end 46.

Figure 3:
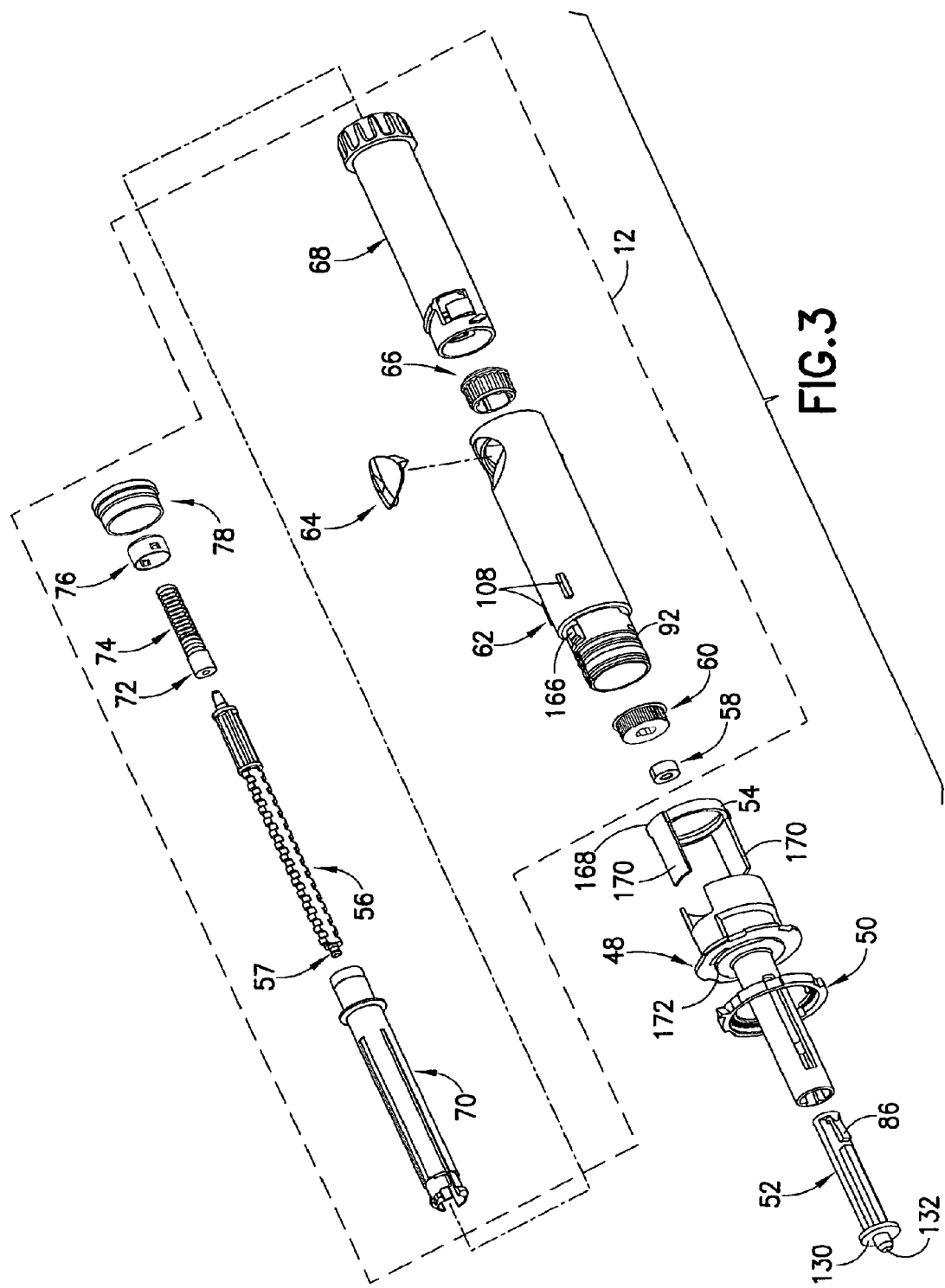
FIG. 3 is an exploded view of a dose-setting mechanism usable with the subject invention, along with a body adapter, release ring, plunger, and locking ring.

The dose-setting mechanism 12 may be of any known pen-type dose mechanism which is adjustable and preferably allows for repeated and consecutive setting of variable-volume doses and administration thereof. Preferably, the dose-setting mechanism 12 includes a cartridge engagement surface 57 extending therefrom (FIG. 3). Preferably, the cartridge engagement surface 57 is defined on the distalmost portion of the dose-setting mechanism 12, such as the distalmost portion of a leadscrew 56 extending from the dose-setting mechanism 12. Leadscrew-type dose-setting mechanisms provide for highly accurate and repeatable dose setting and dose administration of varying volumes.

It is preferred that the dose-setting mechanism 12 be a self-contained unit within the housing 14. In this manner, an "off-the-shelf" dose-setting mechanism can be utilized. With reference to FIG. 3, an exemplary configuration of a dose-setting mechanism 12 is shown. This dose-setting mechanism is generally the same as that disclosed in U.S. Pat. No. 6,248,095, the disclosure of which is incorporated by reference herein. In addition to the leadscrew 56, the dose-setting mechanism 12 may include a spinner 58, a retract nut 60, a body 62, a lens 64, a reset ring 66, a dose set knob 68, a driver 70, and a thumb button 78. The specific configuration and interaction of these elements is discussed in U.S. Pat. No. 6,248,095.

The dose-setting mechanism 12 may additionally include a spring retainer 72, a spring 74, and a spring cap 76. The spring 74 may act as a spacer to ensure that the cartridge engagement surface 57 is located to have sufficient distal movement to cause reconstitution and, optionally initial priming, as described below. In other words, the spring 74 locates the initial start position of the cartridge engagement surface 57 (e.g., by locating the initial start position of the leadscrew 56) and prevents excessive movement proximally of the cartridge engagement surface 57. In addition, the spring 74 acts as a damper upon re-setting of the dose-setting mechanism 12 where the leadscrew 56 is forced proximally to the start position. The spring 74 cushions the return force. The spring retainer 72 and the spring cap 76 act to hold the spring 74 in place by providing end point contacts. As an alternative, the spring 74 can be replaced with a resilient tube 73, such as a silicone tube, as shown in FIG. 3a. Proximal end 75 of the leadscrew 56 can be provided with a protruding finger 77 for holding one end of the resilient tube 73, while a separate holder 79 can be provided for holding the other end of the resilient tube 73. The spring cap 76 can be provided as support for the holder 79. The resilient tube 73 provides the same functions as the spring 74 in cushioning the re-set force and acting as a dimensional spacer.

As will be appreciated by those skilled in the art, other dose-setting mechanisms can be utilized with the subject invention, including various combinations of features of dose-setting mechanisms. For example, U.S. Patent Application Publication No. 2004/0199117 A1, which published on Oct. 7, 2004, shows a "dial-back" feature which allows the user to freely correct a dose without having to reset the dose-setting mechanism. In addition, U.S. Patent Application Publication No. 2004/0127858 A1, which published on Jul. 1, 2004, shows a device having a limiter which prevents setting a dose that is greater than the available medication. The disclosures of these two publications are incorporated by reference herein in their respective entireties.

The dose-setting mechanism 12 is preferably formed to be re-usable (i.e., formed to be used consecutively with multiple drug cartridges or drug cartridge assemblies). It is, thus, preferred that the cartridge engagement surface 57 be re-settable to a start position after the dose-setting mechanism 12 has been used. It should be noted that all or a portion of the cartridge engagement surface 57 may be defined on a distal face of the spinner 58.

By way of non-limiting example, with the configuration of the dose-setting mechanism 12 described above, the leadscrew 56, which defines the cartridge engagement surface 57, extends through the retract nut 60, and the retract nut 60 interacts with the body 62 to preferably selectively permit rotation of the leadscrew 56. With the leadscrew 56 being non-rotatably held by the retract nut 60 relative to the dose-setting mechanism 12, the leadscrew 56 can be translated axially in a distal direction to allow for dose administration. With the retract nut 60 being rotatable, the leadscrew 56 is also rotatable and re-settable in a proximal direction to the start position. Alternatively, the dose-setting mechanism 12 may be a single-use device which is discarded with the completion of a single use, typically, coinciding with the completion of a single drug cartridge. Here, the leadscrew 56 need not be re-settable and can be non-rotatably held in the dose-setting mechanism 12 (e.g., by not permitting rotation of the retract nut 60).

As shown in FIGS. 2 and 3, a body adapter 48, a release ring 50, a plunger 52, and, optionally, a locking ring 54 are mountable onto the dose-setting mechanism 12. With reference to FIGS. 4a and b, the body adapter 48 includes a shaft portion 80 defining a lumen 82 for accommodating the plunger 52. Preferably, a slot 84 is formed in the wall of the shaft portion 80 which is generally straight and parallel to the longitudinal axis of the shaft portion 80, and an angled guide member 86 (FIG. 3) protrudes from the plunger 52 formed to extend into the slot 84 with the plunger 52 being disposed in the lumen 82. The guide member 86 slides along the axial length of the slot 84 with movement of the plunger 52, and the interengagement of the slot 84 and the guide member 86 prevents rotation of the plunger 52 relative to the shaft portion 80.

The body adapter 48 further includes a flange 88 which extends radially outwardly from the shaft portion 80. A retaining wall 90 extends from the flange 88 opposite the shaft portion 80. The retaining wall 90 is formed to be fixed to a distal end 92 of the body 62 (FIG. 3) which also defines a distal end of the dose-setting mechanism 12. The fixing may be of any known type, including an interference fit, bonding, and/or mechanical interaction of locking members. It is preferred that the body adapter 48 be fixed to the dose-setting mechanism 12 such that the two elements may move in concert during operation of the injector device 10. It is further preferred that the body adapter 48 be attached to the dose-setting mechanism 12 so that there is no relative rotation therebetween.

The lumen 82, at the flange 88, is formed to allow passage thereinto of the leadscrew 56 and, optionally, the spinner 58. The leadscrew 56 engages the plunger 52 within the shaft portion 80. The plunger 52 acts to translate force of movement applied thereto by the cartridge engagement surface 57 to the drug cartridge 216. The plunger 52 can be formed of different lengths to accommodate various lengths of the dose-setting mechanism 12 and the drug cartridge 216. With sufficient length of the plunger 52, proper and full reconstitution can be achieved. In addition, proper initial priming can be achieved. As an alternative, the cartridge engagement surface 57 can directly engage the drug cartridge 216, without the use of the plunger 52.

With reference to FIG. 2, a biasing means 94, preferably a spring, is disposed in the housing 14 to urge the dose-setting mechanism 12 from an initial, first position to a second position relative to the housing 14. It is preferred that the biasing means 94 be a coil spring which is sized to pass over the dose-setting mechanism 12 and to have a distal end 95 engage the flange 88 of the body adapter 48. With this arrangement, buckling and other sideward displacement of the biasing means 94 may be limited. A proximal end 96 of the biasing means 94 may be disposed to act against the housing 14. Alternatively, and with the preferred arrangement, a spring seat 98 is provided which is shaped and sized to be accommodated within the rear housing 42. Preferably, the spring seat 98 is non-rotatably fixed in the rear housing 42. The spring seat 98 includes a bearing surface 100 for engagement against the proximal end 96 of the biasing means 94.

A cut-out 102 may be formed in the spring seat 98 to match a cut-out 104 formed in the rear housing 42. The cut-outs 102, 104 are axially alignable to permit a user to view the lens 64 of the dose-setting mechanism 12 in setting a dosage amount on the dose-setting mechanism 12. The lens 64 permits visual inspection of the dose setting. Dose indicia may be provided on the dose set knob 68 which are viewable through the lens 64. As shown in FIG. 5, the spring seat 98 is tubular and includes a passageway 110 therethrough sized to accommodate the dose-setting mechanism 12.

Preferably, the dose-setting mechanism 12 is retained in the first position against the force of the biasing means 94. It addition, it is preferred that the dose-setting mechanism 12 be retained in the first position until released by a trigger. Although any known retaining arrangement and any known trigger configuration are usable with the subject invention, a representative arrangement is depicted and described herein. As shown in FIG. 6, a plurality of inwardly-extending ribs 112 may be disposed along a limited longitudinal length of the interior of the rear housing 42. The flange 88 of the body adapter 48 defines a profile slidable through the interior of the rear housing 42 with slots 114 being formed on the flange 88 corresponding to the number, size and location of the ribs 112 (FIG. 4b). As such, the flange 88 may slide through the rear housing 42 over the ribs 112. Rotation of the flange 88 relative to the rear housing 42 is not desired and the slots 114 may be formed to limit such.

Figure 7A:
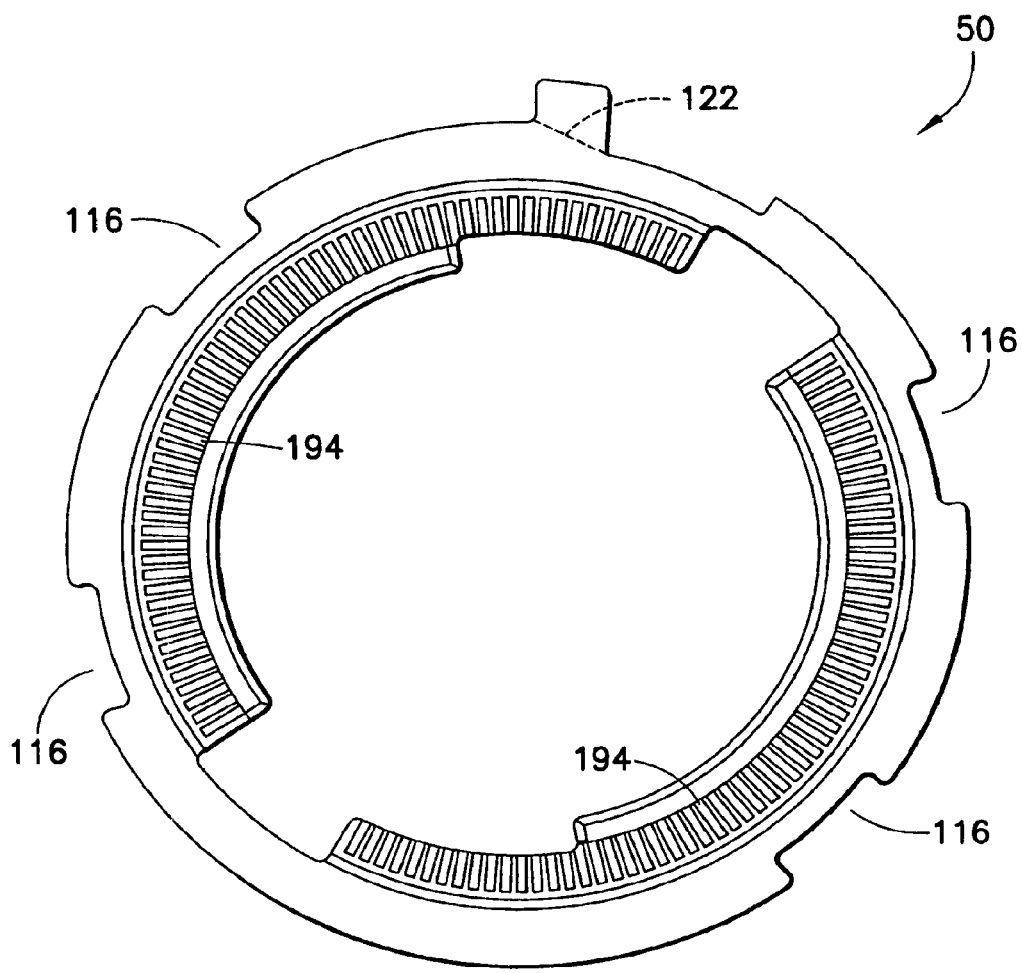
FIGS. 7a and b are respectively top and side views of a release ring.

With the dose-setting mechanism 12 being in the first position, the release ring 50 is interposed between the flange 88 and the ribs 112. With reference to FIG. 7a, the release ring 50 includes a comparable profile to the flange 88, with release slots 116 being formed that are comparably formed and arranged as the slots 114 of the flange 88. In the first position of the dose-setting mechanism 12, the release ring 50 is positioned to have the release slots 116 out of alignment with the ribs 112 of the rear housing 42. With this arrangement, force of the biasing means 94 against the flange 88 is transmitted to the release ring 50. However, the interengagement of the release ring 50 and the ribs 112 counteracts the force and prevents movement of the flange 88. For activation, the release ring 50 is caused to rotate to align the release slots 116 with the ribs 112. As such, the counteraction against the force of the biasing means 94 is removed and the biasing means 94 may urge the flange 88, along with the body adapter 48 and the dose-setting mechanism 12, from the first position.

Figure 7B:
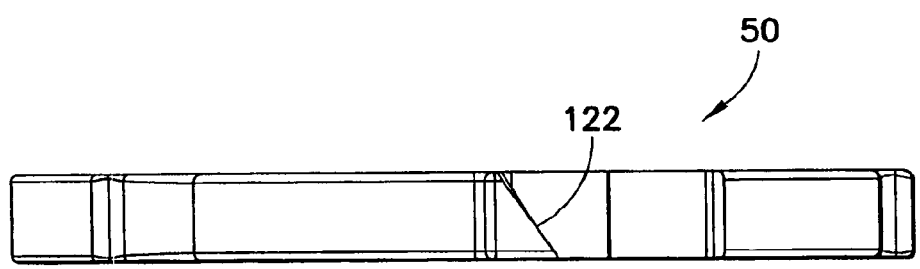
Figure 8:
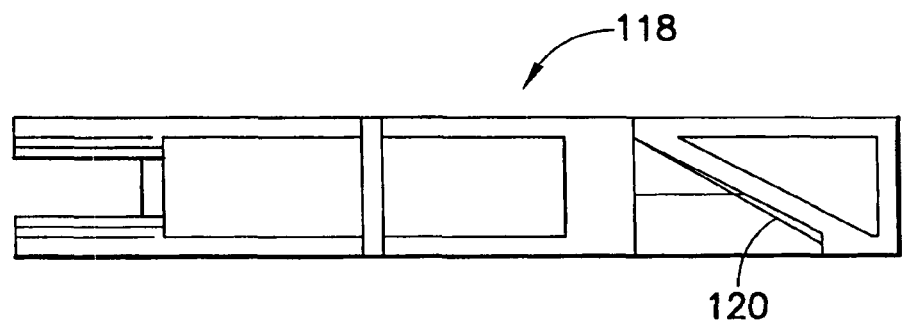
FIG. 8 is a bottom plan view of a release button.
Figure 9:
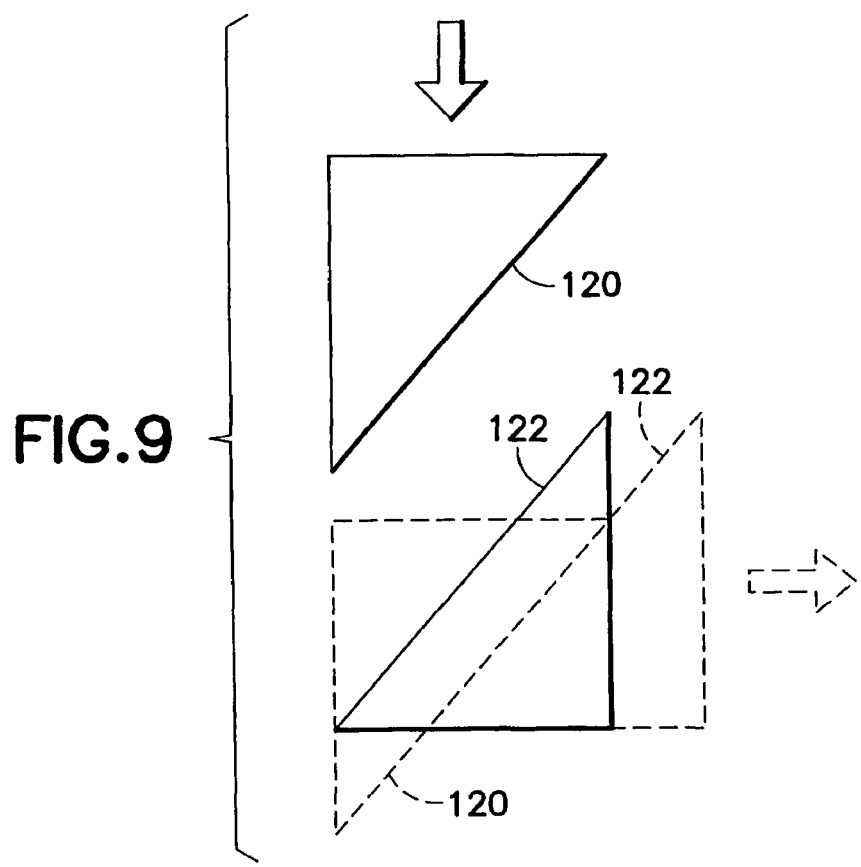
FIG. 9 is a schematic view showing interengagement of the release button and the release ring.

The release ring 50 may be caused to rotate in any known manner. For example, a displaceable release button 118 may be provided which is movably attached to the rear housing 42 (FIG. 2). With reference to FIG. 8, the release button 118 is provided with an angled actuation surface 120. In an initial state, the actuation surface 120 is positioned to be axially aligned, but preferably spaced from, an angled engagement surface 122 formed on the release ring 50 (FIG. 7b). As shown in FIG. 9, with linear displacement of the actuation surface 120 and engagement with the engagement surface 122, the engagement surface 122 is caused to move transversely and create a torque about the release ring 50. This torque results in rotation of the release ring 50. To ensure linear translation of the actuation surface 120, the release button 118 is formed to slide along fixed button slot 124 formed through the rear housing 42. Preferably, release button spring 126 is provided to urge the release button 118 to its initial state, with the actuation surface 120 being spaced from the engagement surface 122. To facilitate handling, outer surface 128 of the release button 118 may be textured to enhance its gripability. As will be appreciated by those skilled in the art, the extent of rotation of the release ring 50 may be controlled by the extent of interengagement of the actuation surface 120 and the engagement surface 122 and the angles of the respective surfaces. The extent of rotation required to align the release slots 116 with the ribs 112 may be achieved by varying these factors.

It is necessary to have the slots 114 of the flange 88 be axially aligned with the ribs 112 with the release ring 50 maintaining the dose-setting mechanism 12 in the first position. If the slots 114 are not axially aligned with the ribs 112, the flange 88 may not pass through the rear housing 42 and proper movement of the dose-setting mechanism 12 may be prevented. Therefore, it is preferred that the spring seat 98 be formed with one or more channels 106 radially spaced about its interior (FIG. 5). Preferably, two of the channels 106 are provided. The channels 106 are spaced and formed to accommodate positioning ribs 108 which extend from the periphery of the dose-setting mechanism 12. As shown in FIG. 3, the positioning ribs 108 may protrude from the body 62. The channels 106 and the positioning ribs 108 are located to interengage with the dose-setting mechanism 12 being in the first position. In addition, the channels 106 and the positioning ribs 108 are located to axially align the slots 114 with the ribs 112. In this manner, with the release ring 50 permitting movement of the dose-setting mechanism 12, as described above, the slots 114 are positioned to slide over the ribs 112. The interengagement of the channels 106 and the positioning ribs 108 also prevents rotation of the dose-setting mechanism 12 with the housing 14. It is further preferred that the channels 106 and the positioning ribs 108 have sufficient lengths to maintain interengagement with the slots 114 initially passing over the ribs 112. As the flange 88 moves distally, the channels 106 and the positioning ribs 108 will disengage.

Figure 10:
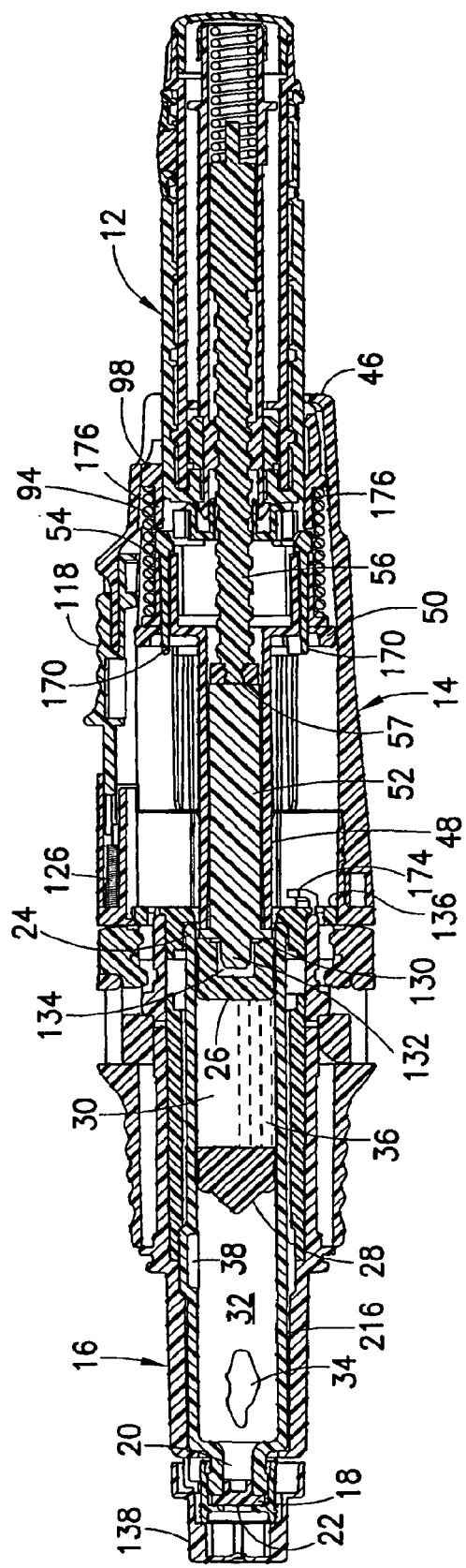
FIG. 10 is a cross-sectional view of the injector device prior to activation with the dose-setting mechanism being in a first position.
Figure 11:
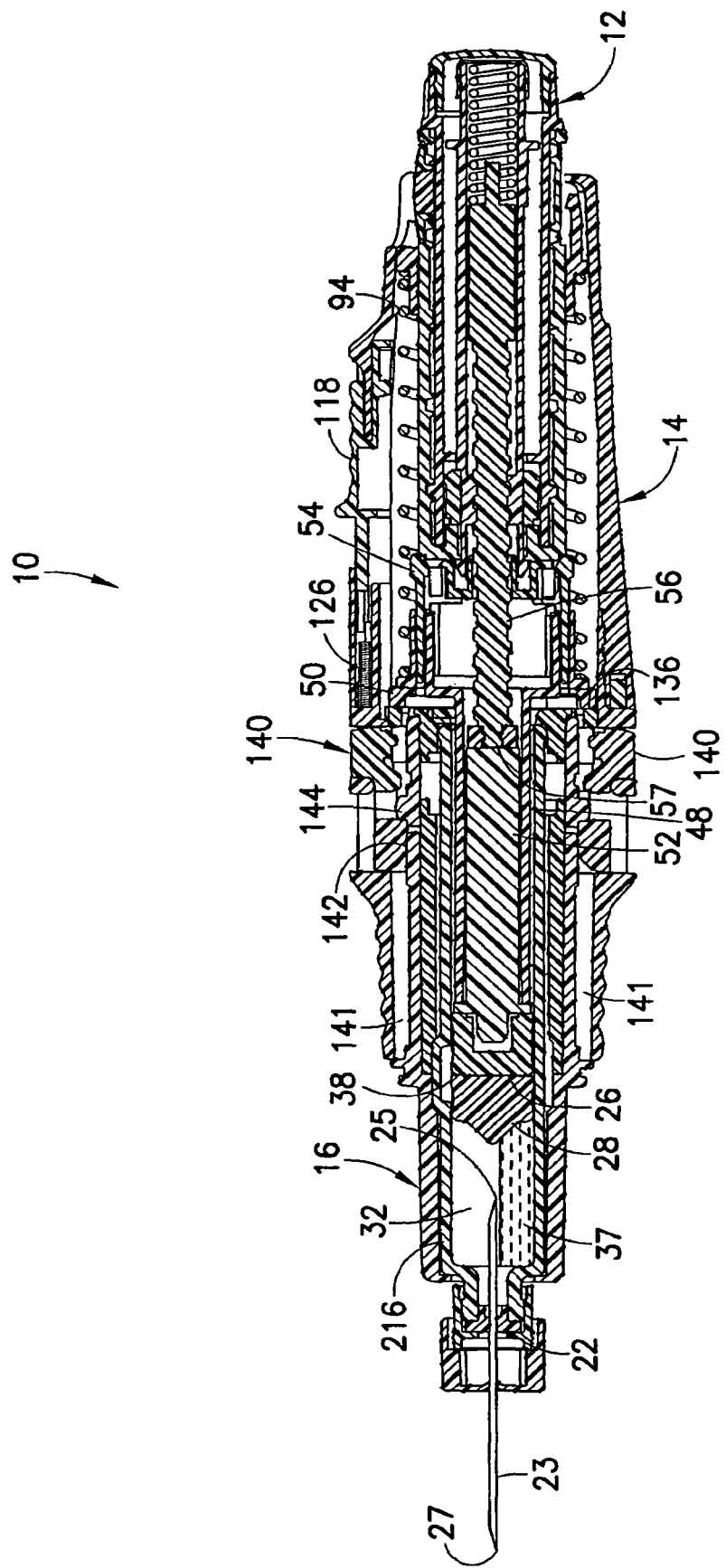
FIG. 11 is a cross-sectional view of the injector device after activation with the dose-setting mechanism being in a second position.

FIGS. 10 and 11 illustrate operation of the injector device 10. Initially, the drug cartridge assembly 16 is inserted through the distal end 44 and attached to the injector device 10. Preferably, the first position of the dose-setting mechanism 12 corresponds to a position which allows the housing 14 to accommodate the drug cartridge 216 being in a full state. As shown in FIG. 10, with the drug cartridge 216 being in a full state, the first stopper 26 is located adjacent to the proximal end 24. With the drug cartridge assembly 16 being secured to the housing 14, distal end 130 of the plunger 52 is positioned to engage the first stopper 26. To ensure a good connection therebetween, the distal end 130 may have a protrusion 132 formed for insertion into a recess 134 in the first stopper 26. In addition, with the first position, the biasing means 94 is compressed and the release ring 50 is in a state of retaining the dose-setting mechanism 12, as described above. As can be seen in FIG. 10, a substantial portion of the dose-setting mechanism 12 extends through the proximal end 46 of the injector device 10.

To cause activation, the release button 118 is displaced relative to the housing 14, resulting in the first and second chambers 30, 32 coming into communication. With the preferred trigger arrangement, displacement of the release button 118 causes the release ring 50 to rotate as described above. This rotation may be achieved through displacement of the release button 118 to its actuation state. As shown in FIG. 11, with the release ring 50 permitting the dose-setting mechanism 12 to move from the first position, the biasing means 94 urges the dose-setting mechanism 12 distally into a second position. The second position is defined by a stop surface 136 within the housing 14. During movement of the dose-setting mechanism 12 from the first position to the second position, the cartridge engagement surface 57 moves across a predetermined distance which, in turn, causes the first stopper 26 to move. The cartridge engagement surface 57, however, does not move relative to the dose-setting mechanism 12 with the dose-setting mechanism 12 moving from the first position to the second position. Movement of the first stopper 26 can cause reconstitution of a drug substance (e.g., lyophilized substance 34) located in the drug cartridge 216, as described above. It is preferred that the second position be defined so that the predetermined distance the cartridge engagement surface 57 traverses is sufficient to allow for reconstitution of the drug substance within the drug cartridge 216. For example, the predetermined distance is sufficient to urge the second stopper 28 into a position sealing the second chamber 32 from the communication channel 38 at the end of the reconstitution process. The predetermined distance can be provided with additional length beyond that necessary for the reconstitution process to initiate, and even to complete, initial priming of the injector device 10. Initial priming can also be achieved by manual operation of the dose-setting mechanism 12 after reconstitution.

During the course of reconstitution, it is preferred that the needle cannula 23 be mounted to the drug cartridge assembly 16 and/or to the housing 14 to act as a vent and permit any trapped gases to escape from the second chamber 32. The rate of venting will affect the rate of reconstitution. In particular, a smaller gauge needle cannula 23 will provide a higher level of resistance against movement of the dose-setting mechanism 12 during reconstitution, and, thus, will provide a slower rate of reconstitution than a larger gauge needle cannula. In addition, the spring constant of the biasing means 94 may be selected to affect the rate of reconstitution, as well as, adjustment of surface interfaces which generate frictional forces resisting the force applied to achieve reconstitution (e.g., frictional forces between the first stopper 26 and the drug cartridge 216 can be adjusted by selection of materials or providing lubricant therebetween).

As an alternative, the injector device 10 can be configured to cause reconstitution without the needle cannula 23 being mounted thereto. Here, the spring force of the biasing means 94 can be selected so as to provide sufficient force to compress any air trapped in the chambers 30, 32 and to force the diluent 36 into the second chamber 32. Without venting, the reconstituted substance 37 will be pressurized in the second chamber 32. Upon mounting the needle cannula 23, the needle cannula 23 will vent the second chamber 32, thereby releasing the trapped pressure and forcing the reconstituted substance 37 into the needle cannula 23. This process may partially or completely achieve initial priming. Full priming can be manually achieved by manual operation of the dose-setting mechanism 12. In addition, the elements of the injector device 10 can be selected and configured so that equilibrium between the pressurized reconstituted substance 37 and the spring force of the biasing means 94 can be achieved with the dose-setting mechanism 12 being in its second position. In this case, upon mounting the needle cannula 23 and venting the second chamber 32, the pressure in the second chamber 32 will be released. The biasing means 94 may be configured to urge the dose-setting mechanism 12 to a third position. Movement to the third position may cause full and automatic initial priming.

The drug cartridge assembly 16 may be initially provided with a removable cap 138 for covering the opening 20 during shipment. The cap 138 is removable to allow for mounting of the needle cannula 23.

With the dose-setting mechanism 12 being in the second position as shown in FIG. 11, and the reconstituted substance 37 being disposed in the second chamber 32, the dose-setting mechanism 12 can be adjusted to select a desired dose of particular volume. With the desired dose being set, the dose-setting mechanism 12 may be actuated which results in the cartridge engagement surface 57 being moved distally relative to the dose-setting mechanism 12, a distance corresponding to the volume of the desired dose. In turn, the first stopper 26 moves the corresponding distance. This movement results in the desired dose being expelled from the second chamber 32 via the needle cannula 23. Dosing may be repeated as needed with varying volumes being provided.

Upon depletion of the contents of the drug cartridge 216, the drug cartridge assembly 16 may be separated from the housing 14 and discarded. If the injector device 10 is a single-use type, the injector device 10 may be discarded also with the drug cartridge assembly 16. If the injector 10 is re-usable, the dose-setting mechanism 12 is returned to the first position, and the leadscrew 56 is reset to its initial position, as discussed below.

Figure 12:
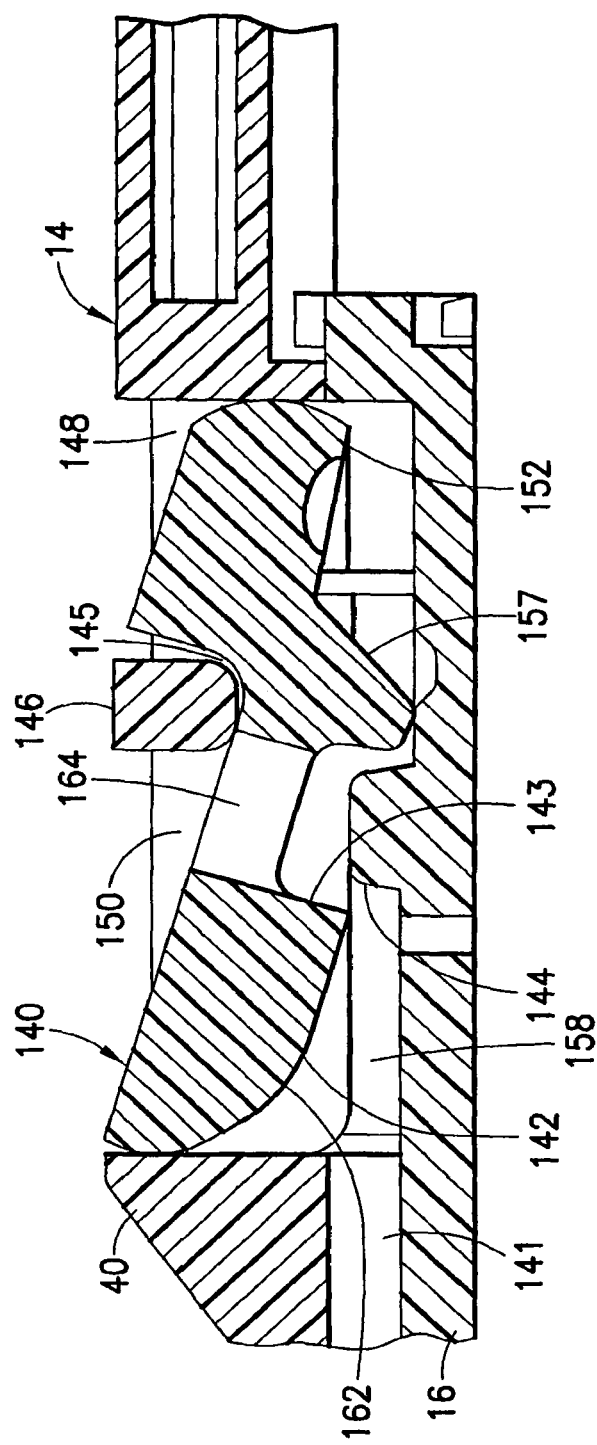
FIG. 12 is a partial cross-sectional view showing a cartridge release button in a release position.

Optionally, a releasable attachment may be provided for securing the drug cartridge assembly 16 to the housing 14. In this manner, the injector device 10 may be re-usable with replacement of a spent drug cartridge 216. For example, one or more cartridge release buttons 140 may be formed to be releasably attached to the drug cartridge assembly 16 to the housing 14. It is preferred that two of the release buttons 140 be provided and located at diametrically opposed locations on the housing 14 to provide even holding force for the drug cartridge assembly 16. With reference to FIGS. 11 and 12, the cartridge release buttons 140 are displaceable between release and locking positions. In a locking position (FIG. 11), each of the cartridge release buttons 140 is positioned to interferingly engage a protrusion 144 extending from the drug cartridge assembly 16 upon distal movement of the drug cartridge assembly 16 relative to the housing 14, thereby inhibiting separation of the drug cartridge assembly 16 from the housing 14. In particular, a distal end 142 of the cartridge release button 140 is positioned to interferingly engage the protrusion 144. The protrusions 144 may be formed with various configurations but are preferably cylindrical so that precise axial alignment of the protrusions 144 and the cartridge release buttons 140 may be avoided. Slots 141 may be provided to guide the protrusions 144 to the cartridge release buttons 140 and ensure sufficient axial alignment therebetween for locking engagement. The slots 141 extend from the distal end 44 of the front housing 40 (FIG. 2).

In a release position as shown in FIG. 12, each of the cartridge release buttons 140 does not interferingly engage the protrusion 144 upon distal movement of the drug cartridge assembly 16 relative to the housing 14, thereby facilitating separation of the drug cartridge assembly 16 from the housing 14. The distal ends 142 may be provided each with a shoulder 143 or other cut-out to provide an engaging surface against the protrusion 144. Preferably, the shoulder 143 is disposed generally perpendicularly to the distal direction of movement of the drug cartridge assembly 16.

Preferably, each of the cartridge release buttons 142 is pivotally mounted to the front housing 40 to permit displacement. Two openings 148, 150 are defined on the sides of a cross-piece 146 in the front housing 40. The cartridge release button 142 includes a notch 145 for pivotal engagement with the cross-piece 146. The cartridge release button 142 is disposed interiorly of the rear housing 40 with the notch 145 being below the cross-piece 146. The first opening 148 permits access to depress a proximal end 152 of the cartridge release button 142. Upon being depressed, the cartridge release button 140 pivots about the cross-piece 146 with the distal end 142 moving away from the drug cartridge 16 to the release position.

Preferably, a deflectable spring 154 is provided to urge each of the cartridge release buttons 140 to its locking position. In particular, the spring 154 is positioned to bias the proximal end 152 of the cartridge release button 140 away from the drug cartridge assembly 16. To facilitate mounting of the spring 154 within the housing 14, a front housing shell 156 may be provided which is mountable into the front housing 40 and provides support for the springs 154. The shell 156 is formed with an interior to accommodate the drug cartridge assembly 16. Channels 158 are formed through the shell 156 to allow the cartridge release buttons 140 to extend therethrough and engage the drug cartridge assembly 16. A stop arm 157 may extend from the cartridge release button 140 to engage a portion of the shell 156. This engagement limits rotation of the cartridge release button 140 under force of the spring 154. An internal stop surface (not shown) may also be provided on the shell 156 to limit proximal insertion of the drug cartridge 16 thereinto. In addition, the stop surface 136 may be defined on a proximal end 160 of the shell 156 to define the second position of the dose-setting mechanism 12. The shell 156 is fixed to the first housing 40 using any known technique.

It is further preferred that the distal end 142 be formed with a tapered or rounded end 162. With proximal movement of the drug cartridge assembly 16 into the housing 14 during insertion thereof, the protrusion 144 engages the distal end 142 and may force the cartridge release button 140 in its release position, thus, allowing the protrusion 144 to pass thereby. With the protrusion 144 passing thereby, the cartridge release button 140 returns to its locking position. To allow a user visual inspection of the inserted drug cartridge, an aperture 164 may be formed through each of the cartridge release buttons 140. Together with the opening 150 and the channel 158, the aperture 164 provides visual access to the drug cartridge assembly 16 in an attached position. Locking means for preventing inadvertent detachment of the drug cartridge assembly 216 may be provided for the cartridge release buttons 140. For example, the locking means may be required to be unlocked to permit detachment of the drug cartridge assembly 216.

As described above, and as a further optional feature, the injector device 10 may include a feature for selectively preventing rotation of the leadscrew 56. With this feature, the leadscrew 56 may be prepared for actuation and be allowed to be re-set. With reference to the exemplary configuration of the dose-setting mechanism 12 described above, selective prevention of rotation of the leadscrew 56 can be achieved where the retract nut 60 is caused to be selectively non-rotatably fixed and released depending on circumstances. With the injector device 10, one or more tabs 166 (FIG. 3) may be formed in the body 62 to non-rotatably hold the retract nut 60, as described in U.S. Pat. No. 6,248,095. The tabs 166, however, require inward deflection to be activated. To achieve such inward deflection, the locking ring 54 is provided with an annular body 168 formed to slide onto the distal end 92 of the body 62 and over the tabs 166, thereby causing inward deflection thereof. It is desired that the locking ring 54 cause inward deflection of the tabs 166 with the dose-setting mechanism 12 being in the second position. This allows for the retract nut 60 to be not rotatable in the second position of the dose-setting mechanism 12, with the leadscrew 56 also not being rotatable and the leadscrew 56 being drivable distally to cause a dosage administration.

It is also desired to have the annular body 168 be disengaged from the tabs 166 with the dose-setting mechanism 12 being in the first position. As such, this arrangement permits rotation of the leadscrew 56 and re-setting thereof to an initial position. This would also prevent use of the dose-setting mechanism 12 in the first position, prior to reconstitution.

To allow for selective engagement and disengagement of the locking ring 54, legs 170 are provided which extend from the annular body 168 and are formed to pass through passages 172 in the body adapter 48 (FIG. 4*b*). The legs 170 have sufficient length to extend distally out from the flange 88 in an initial state, with the tabs 166 being not deflected (FIG. 2). Stops 174, corresponding to the legs 170 of the locking ring 54, protrude from the distal end 160 of the shell 156. The stops 174 are positioned to not obscure the stop surface 136, but are positioned to axially engage the legs 170. With movement of the dose-setting mechanism 12 from the first position to the second position, the stops 174 engage the legs 170 and cause the locking ring 54 to be held in a fixed position for the final length of the movement between the first and second positions. Accordingly, the annular body 168 is forced onto the moving dose-setting mechanism 12, and, more particularly, onto the tabs 166. With engagement of the tabs 166, the dose-setting mechanism 12 can be actuated.

For disengagement of the locking ring 54, one or more extensions 176 extend from the spring seat 98 which are formed to hold the locking ring 54 in a fixed position upon proximal movement of the dose-setting mechanism 12 from the second position to the first position. The extensions 176 hold the locking ring 54 in a fixed position for the final length of the movement, thus, forcing the locking ring 54 off of the tabs 166 and returning the locking ring 54 to its initial position. The dose-setting mechanism 12 is then not actuatable.

The injector device 10 can be re-set using various techniques, and possibly special tools. Re-setting may require not only moving the dose-setting mechanism 12 from the second position, but also re-setting the cartridge engagement surface 57 to its initial position. With reference to FIGS. 13 a-g, a mandrel 178 is shown that may be inserted into the housing 14 to cause movement of the dose-setting mechanism 12 from the second position to the first position to re-set the injection device 10, where preferably the retaining arrangement acts to hold the dose-setting mechanism 12 in the first position. The mandrel 178 may also force the leadscrew 56 to its initial position. The mandrel 178 may be further formed with various features which also permit rotation of the release ring 50 to an initial position with the engagement surface 122 being axially aligned with the actuation surface 120.

With reference to FIGS. 13*a-g*, the mandrel 178 includes a base 180 and an upstanding shaft portion 182 extending therefrom. The base 180 is sized and shaped to provide the mandrel 178 with sufficient stability to stand vertically as shown in FIGS. 13*a-e*. The shaft portion 182 is generally cylindrical and formed with an outer diameter smaller than the opening in the distal end 44 to permit insertion of the shaft portion 182 into the injector device 10. Preferably, the base 180 is formed larger than the opening in the distal end 44 so as to act as a stop against excessive insertion.

The shaft portion 182 includes at least one protruding locator pin 184, preferably two diametrically opposed locator pins 184, extending radially from the shaft portion 182. The locator pins 184 are positioned and formed to slide into the slots 141 formed in the front housing 40. To ensure proper alignment of the shaft portion 182 within the injector device 10, the locator pins 184 are sized only to permit insertion with the locator pins 184 being in the slots 141 (i.e., insertion is prevented where the locator pins 184 are not aligned with the slots 141).

At the free end of the shaft portion 182, interrupted flange portions 186 extend radially outwardly having breaks 188 defined therebetween. The flange portions 186 each include a generally flat top portion 190 on which is formed teeth 192. The teeth 192 are formed to shape matingly engage ratchet teeth 194 formed on the release ring 50 (FIG. 7a) so that when engaged rotation of the mandrel 178 will result in rotation of the release ring 50. As will be appreciated by those skilled in the art, any set of cooperating members can be used which will permit a clutching-type action and simultaneous rotation.

One or more re-set channels 196 are formed on the side of the shaft portion 182, each extending from one of the breaks 188. Preferably, two of the re-set channels 196 are provided. The re-set channels 196 are each defined by spaced-apart straight guide wall 198 and configured guide wall 200. With reference to FIG. 13 d, the straight guide wall 198 is preferably aligned to extend from one end of the associated break 188 and is generally parallel to a longitudinal axis of the shaft portion 182. The configured guide wall 200 includes a first, generally straight portion 202 and a second divergent portion 204. The straight guide wall 198 and the second divergent portion 204 of the configured guide wall 200 define an enlarged pocket 206 of the re-set channel 196. All of the enlarged pockets 206 formed about the shaft portion 182 are preferably aligned to radially extend in the same direction. In other words, with looking at the circumference of the shaft portion 182, all of the enlarged pockets 206 preferably extend away from the associated straight guide wall 198 in the same angular direction (clockwise or counter-clockwise).

The re-set channels 196 are formed to accommodate the stops 174 in sliding engagement. The stops 174 are preferably inwardly directed in extending from the shell 156. The interengagement of the locator pins 184 and the slots 141 allows for axial alignment of the stops 174 and the re-set channels 196. With insertion of the mandrel 178 into the injector device 10, the stops 174 slide within the re-set channels 196; the straight guide wall 198 and the first straight portion 202 of the configured guide wall 200 prevent relative rotation between the mandrel 178 and the injector device 10 for a predetermined length of movement. Upon traversing the predetermined length of movement, the stops 174 reach the enlarged pockets 206, where rotation between the mandrel 178 and the injector device 10 is permitted.

Figure 13A:
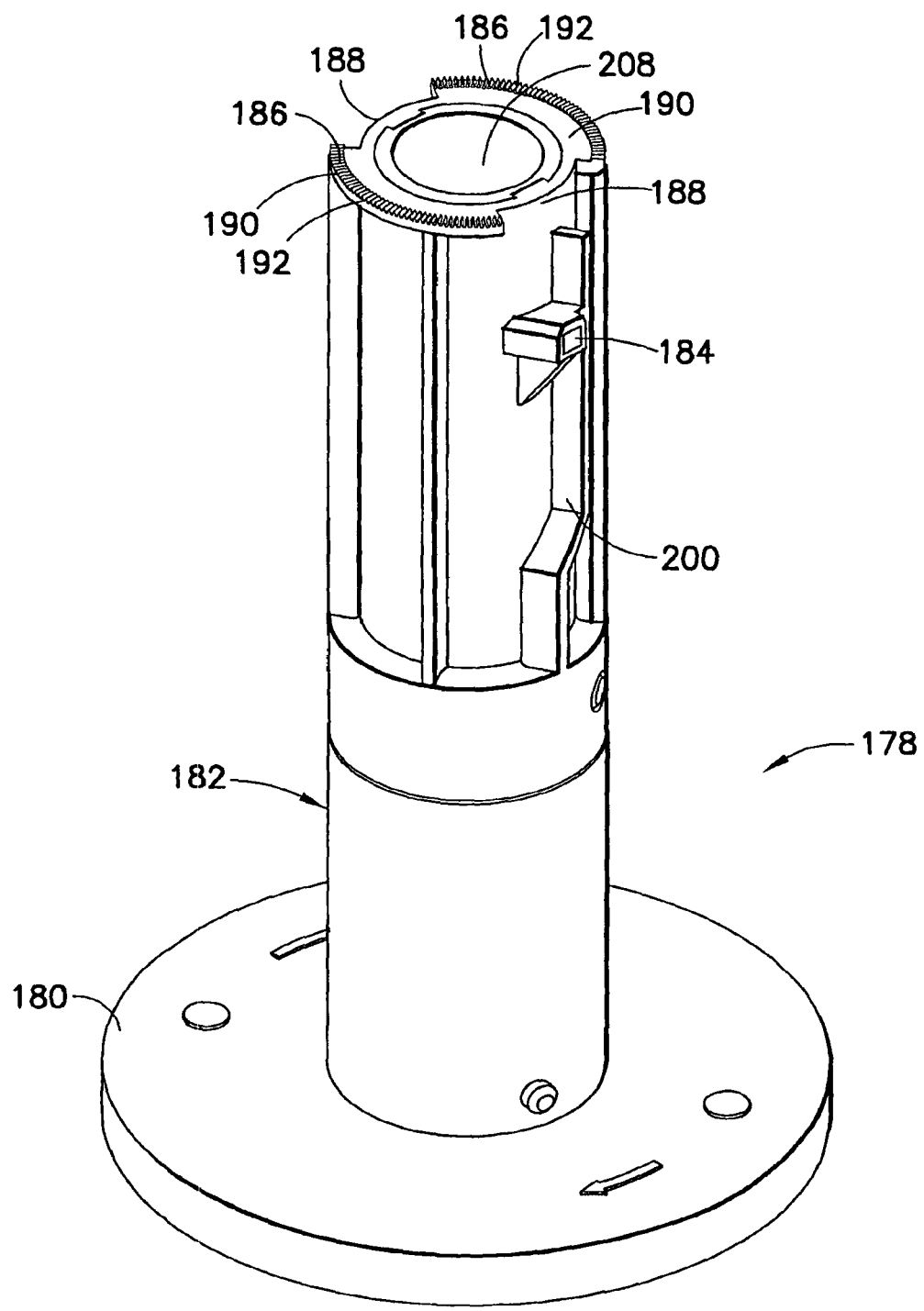
FIGS. 13a-g are various views of a mandrel useable with the injector device of the subject invention to cause re-setting thereof; and, FIGS. 14-16 depict various stages of a re-setting process of the subject invention.
Figure 13B:
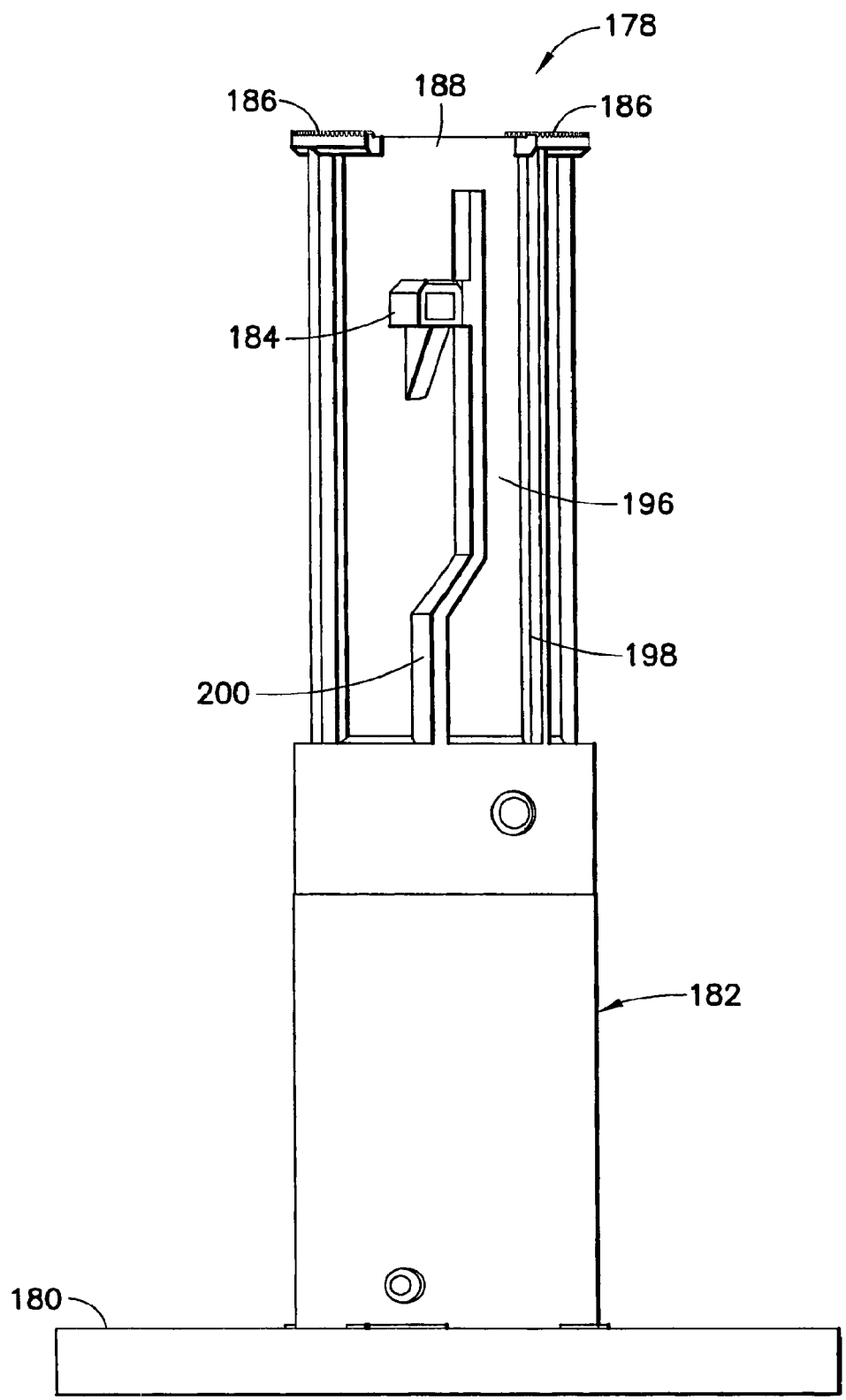
Figure 13C:
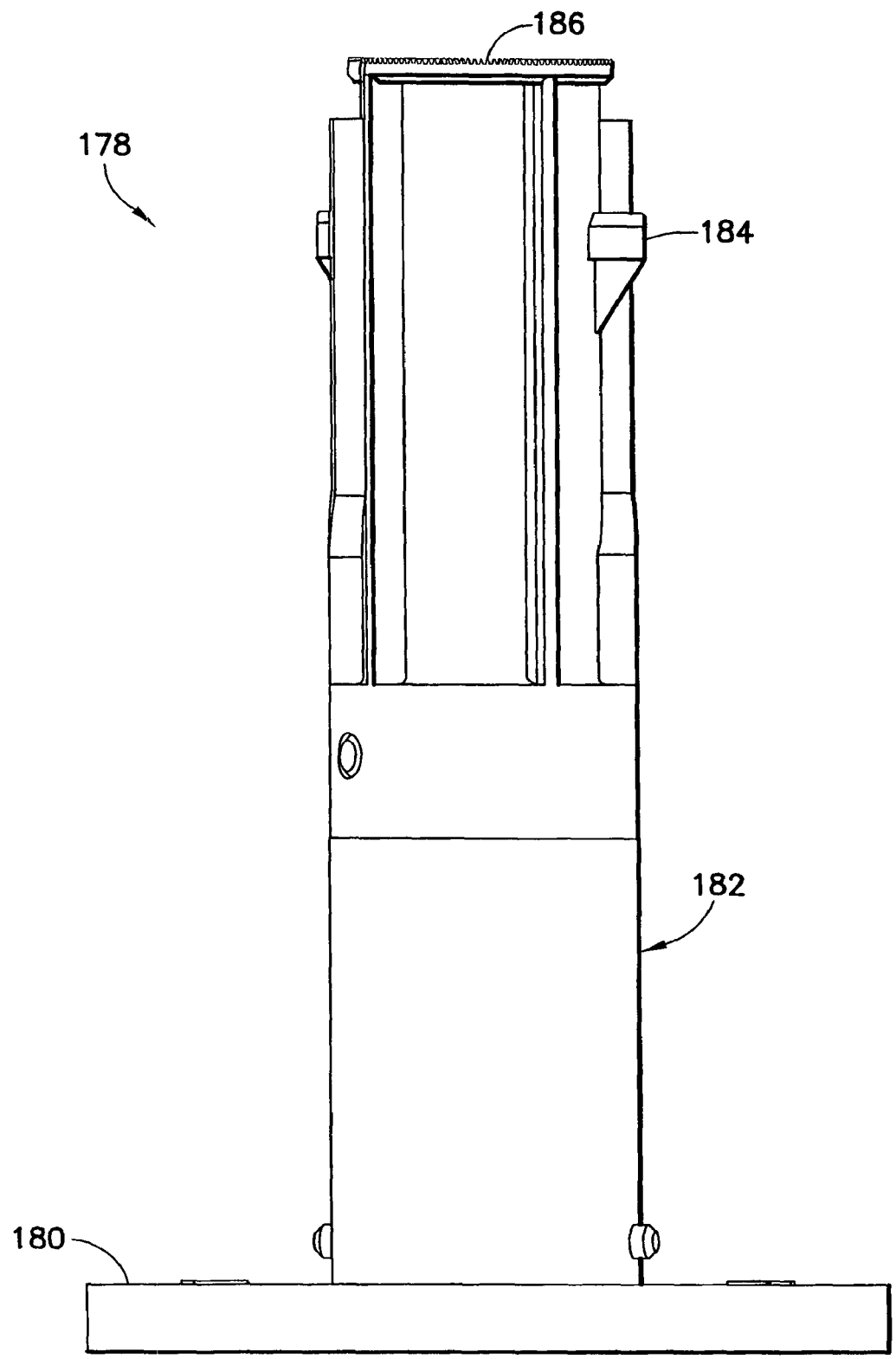
Figure 13D:
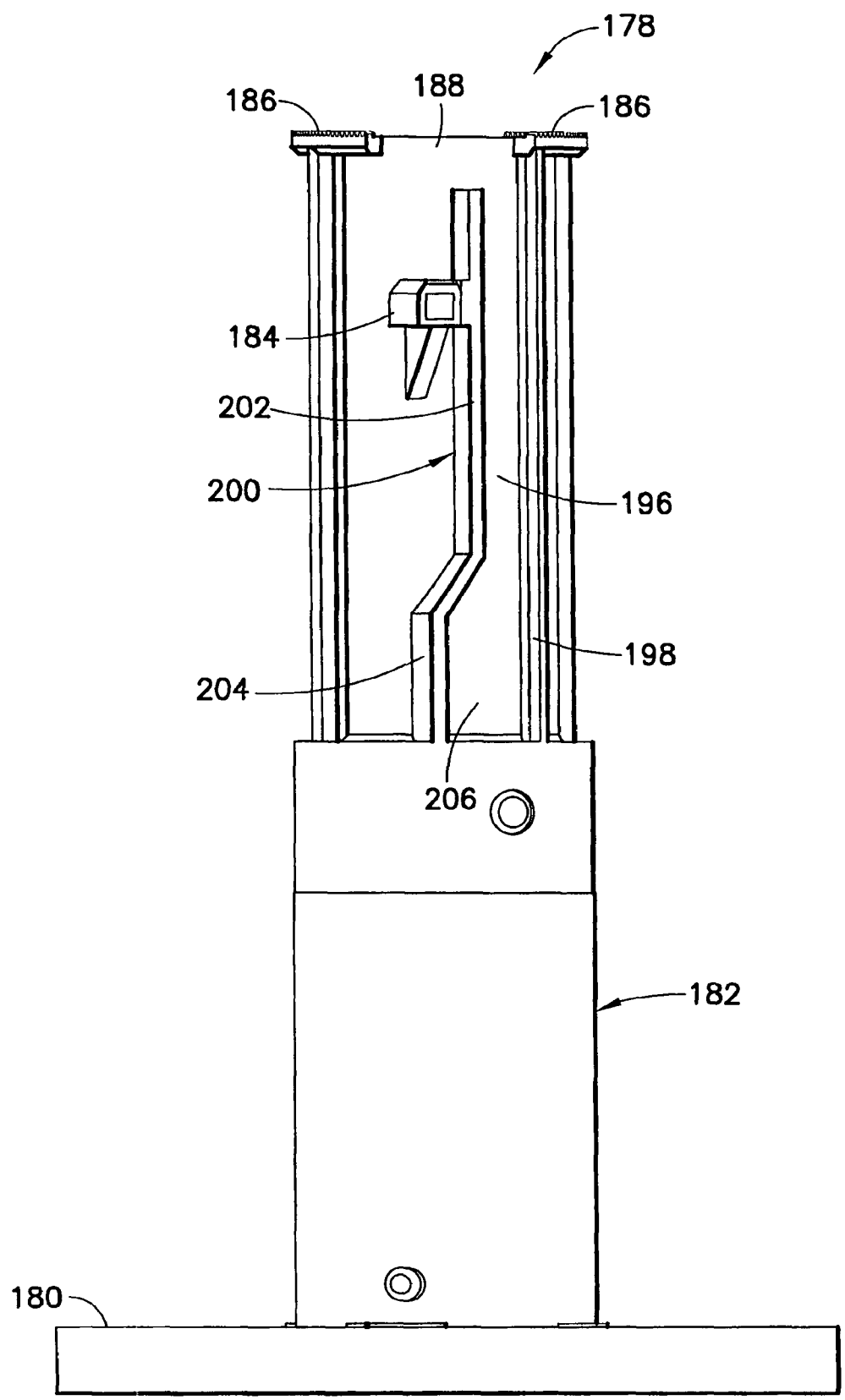
Figure 13E:
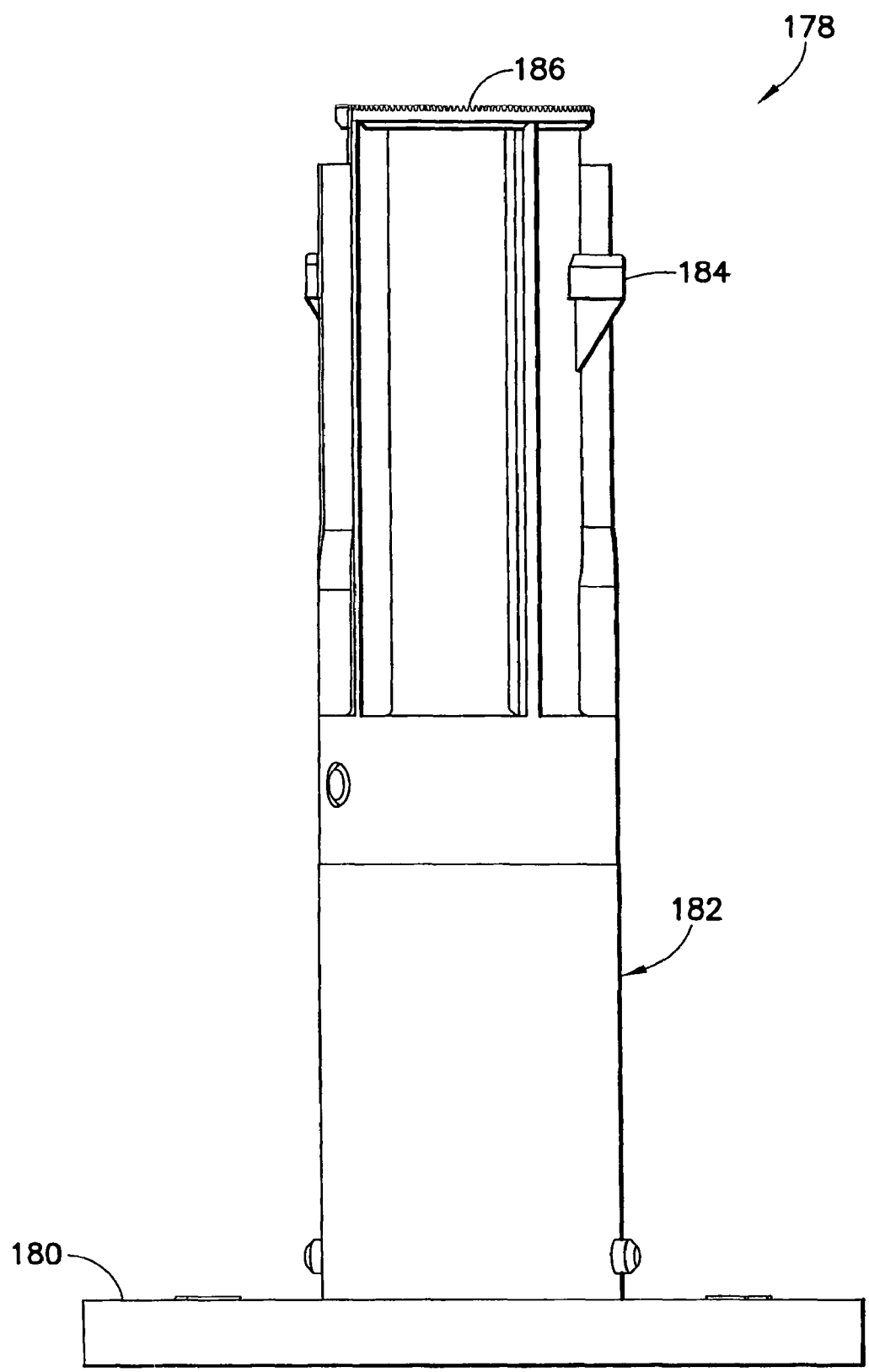
Figure 13F:
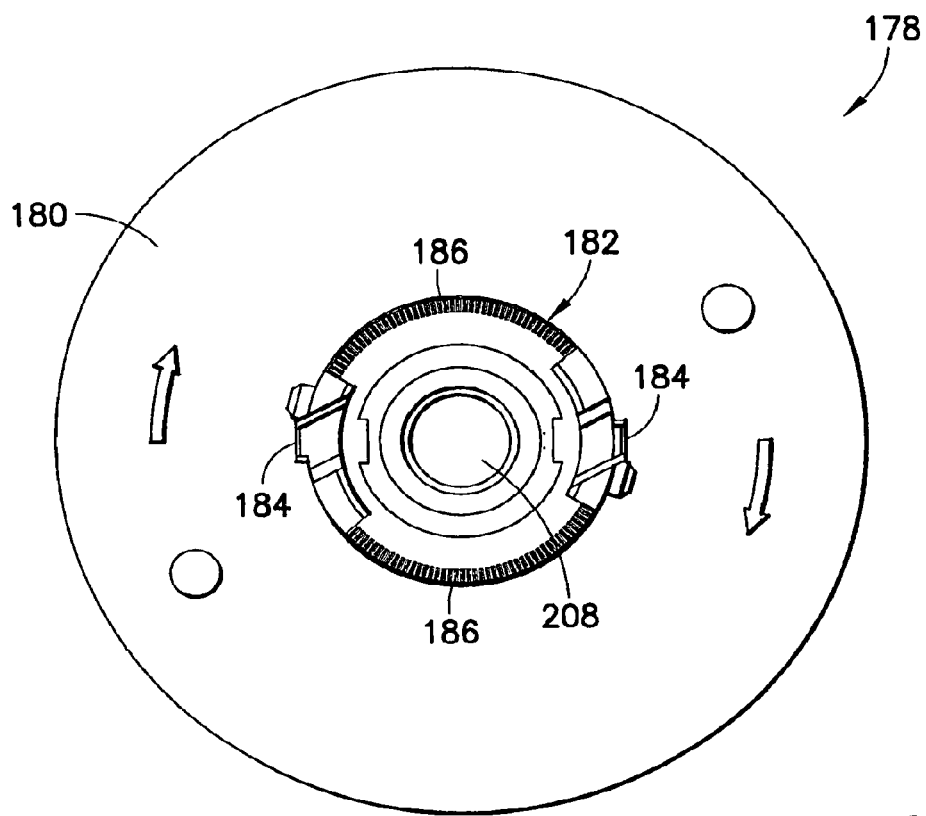
Figure 13G:
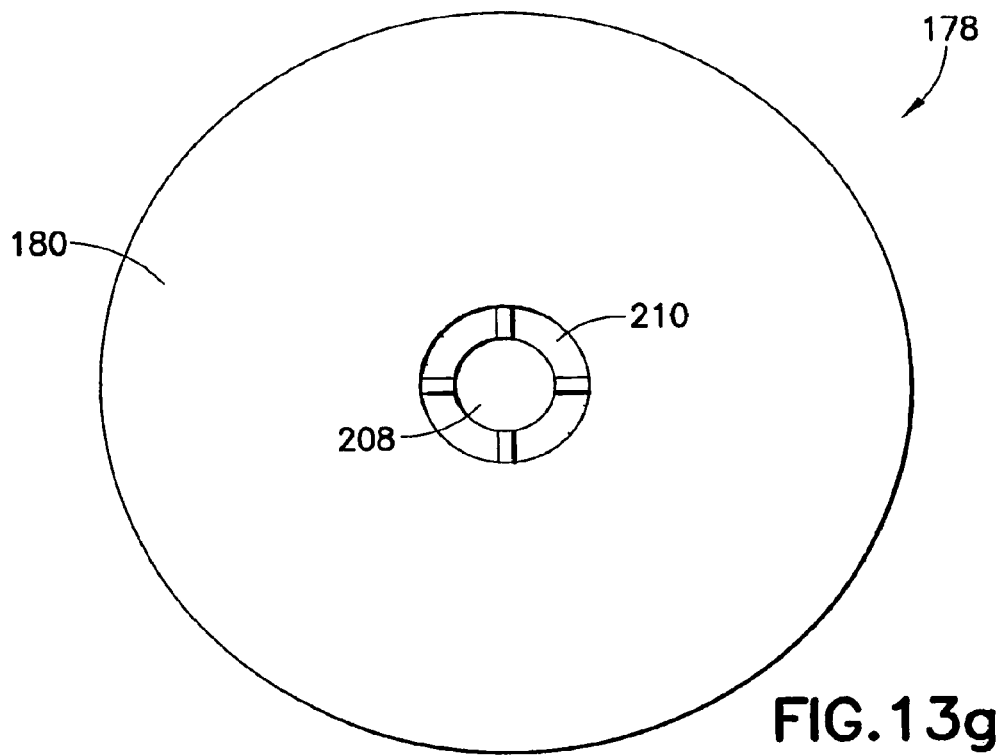

It is also preferred that the shaft portion 182 define an inner lumen 208 sized to accept insertion of the shaft portion 80 of the body adapter 48 (FIGS. 13f and 13g). The inner lumen 208 preferably extends the full length of the mandrel 178 and is open at both ends. An inwardly extending ridge 210 is formed at a mid-point of the inner lumen 208. The ridge 210 is annular in shape and formed with a smaller diameter than the shaft portion 80 to bear against the plunger 52 (or the cartridge engagement surface 57 if the plunger 52 is not utilized).

The shaft portion 182 is formed with sufficient length to forcibly urge the dose-setting mechanism 12 from the second position to the first position. In addition, the ridge 210 is located to urge the leadscrew 56 to a start position. As such, the injector device 10 is re-settable to permit a further automatic reconstitution and is re-settable to have the dose-setting mechanism 12 back to its start position.

Figure 14:
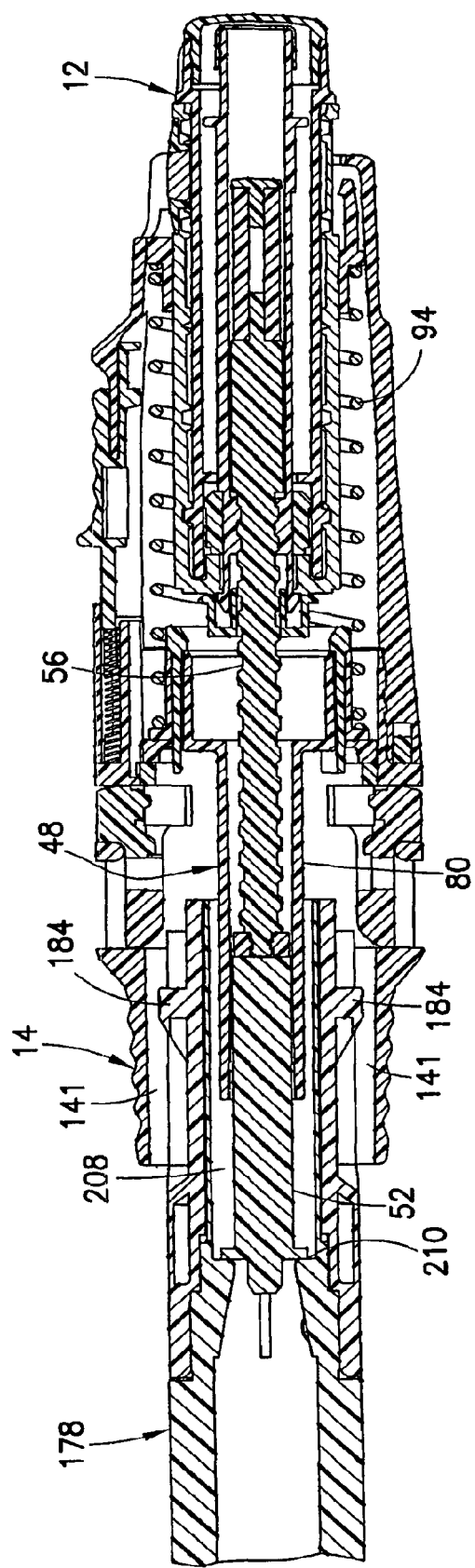
Figure 15:
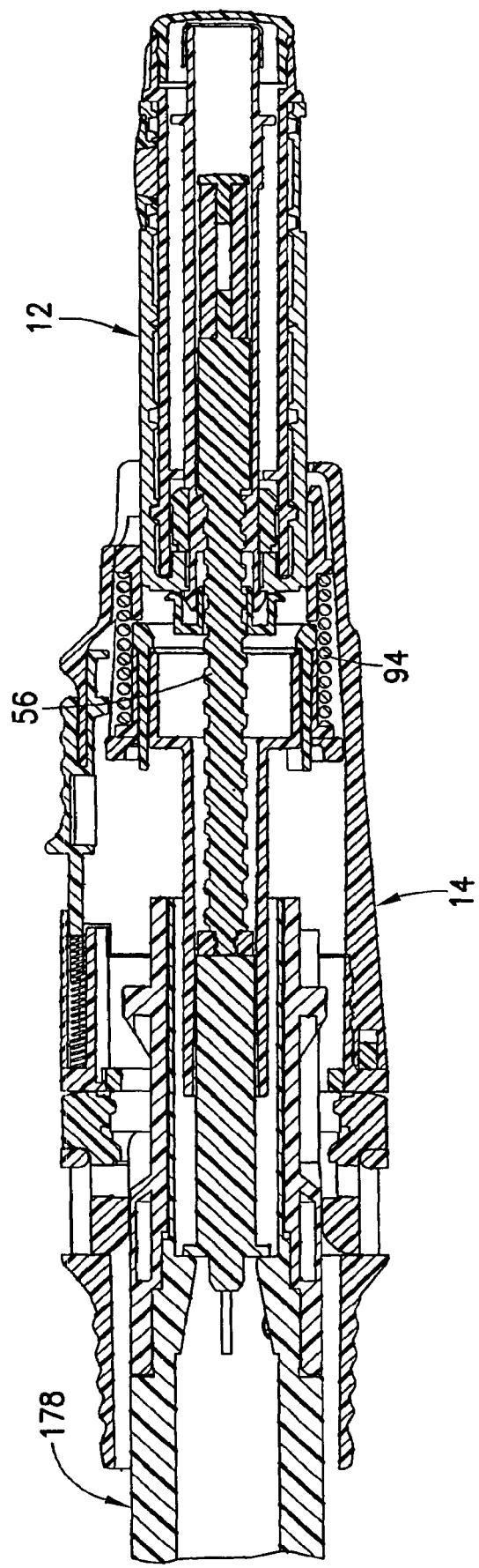
Figure 16:
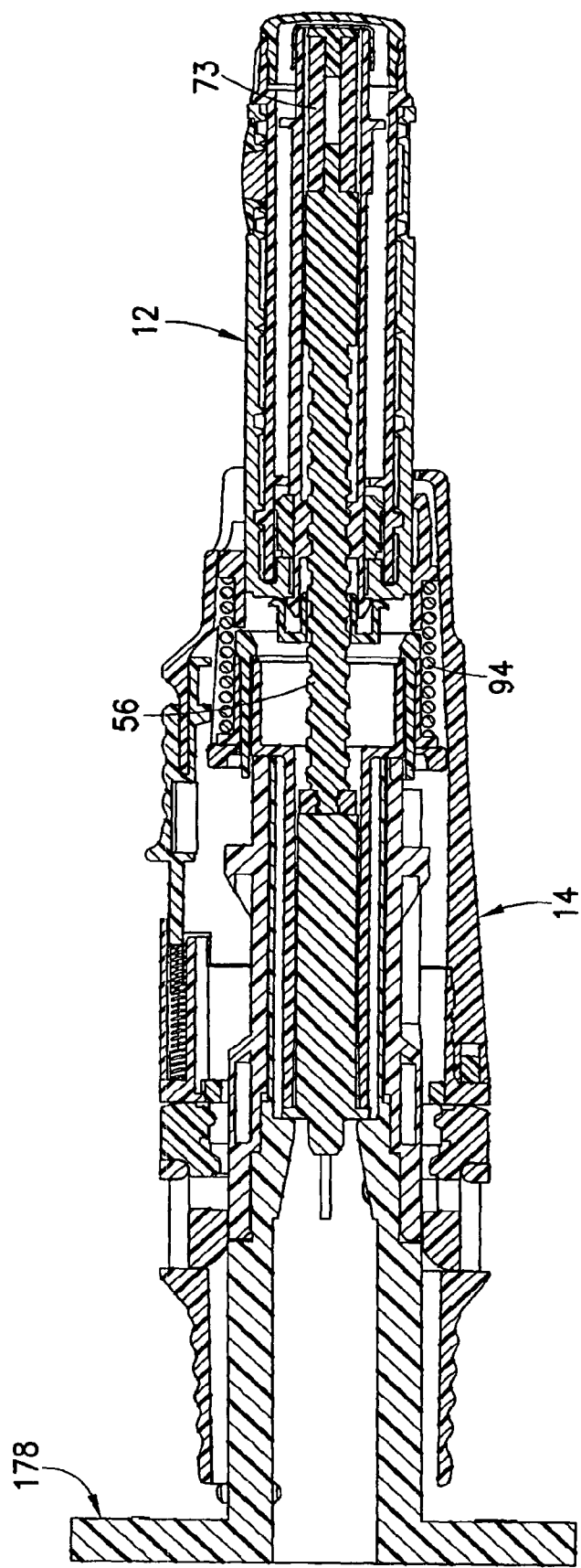

With reference to FIGS. 14-16, a re-setting process is depicted. With the drug cartridge assembly 16 not being present in the housing 14, the mandrel 178 is inserted into the housing 14 with the locator pins 184 sliding along the slots 141. With insertion, the shaft portion 80 of the body adapter 48 is received within the inner lumen 208 with the plunger 52 engaging the ridge 210. Further insertion causes the dose-setting mechanism 12 to retract proximally against the force of the biasing means 94. With the dose-setting mechanism 12 still being outside of the first position, the leadscrew 56 is non-rotatably fixed and, thus, is not movable proximally relative to the dose-setting mechanism 12. Accordingly, the leadscrew 56 transmits the force applied to the plunger 52 to the dose-setting mechanism 12 until the dose-setting mechanism 12 is forced to the first position, as shown in FIG. 15. At this point, the leadscrew 56 is released and allowed to rotate, as described above, whereby further insertion of the mandrel 178 into the housing 14 causes the leadscrew 56 to move proximally to its start position, as shown in FIG. 16. The spring 74/resilient tube 73 limits the proximal movement of the leadscrew 56 relative to the dose-setting mechanism 12.

With the dose-setting mechanism 12 and the leadscrew 56 having been urged to their respective start positions, the mandrel 178 is fully inserted into the housing. Here, the teeth 192 of the flange portions 186 engage the ratchet teeth 194 of the release ring 50. The mandrel 178 is caused to rotate with the release ring 50 also rotating. As a result, the release slots 116 are taken out of alignment with the ribs 112, and the dose-setting mechanism 12 is releasably retained, as described above. The configuration of the enlarged pockets 206 will only permit rotation in one direction, to ensure that the release ring 50 is properly situated for later actuation. The mandrel 178 is then removed, and the housing 14 is ready to receive a drug cartridge assembly 216.

While the invention has been described in relation to the preferred embodiments with several examples, it will be understood by those skilled in the art that various changes may be made without deviating from the spirit and scope of the invention as defined in the appended claims.

What is claimed is:

1. An injector device for automatic reconstitution of a substance comprising:
   a dose-setting mechanism having a cartridge engagement surface extending therefrom, said dose-setting mechanism being adjustable to set a dose for the injector device;
   a housing cooperatively engaging said dose-setting mechanism;
   a spring for selectively moving said dose-setting mechanism from a first position to a second position relative to said housing, said cartridge engagement surface moving a predetermined distance relative to said housing with said dose-setting mechanism moving from said first position to said second position; and,
   a needle, said needle being fixed relative to said housing so that there is no relative movement between said needle and said housing with said dose-setting mechanism moving from said first position to said second position.

2. An injector device as in claim 1, further comprising means for releasably attaching a drug cartridge to said housing.

3. An injector device as in claim 1, wherein said cartridge engagement surface does not move relative to said dose-setting mechanism with said dose-setting mechanism moving from said first position to said second position.

4. An injector device as in claim 1, wherein said dose-setting mechanism is actuatable to urge doses from the injector device with said dose-setting mechanism being located in said second position.

5. An injector device as in claim 4, wherein said dose-setting mechanism is not actuatable to urge doses from the injector device with said dose-setting mechanism being located in said first position.

6. An injector device as in claim 1, further comprising means for releasably retaining said dose-setting mechanism in said first position against said biasing means.

7. An injector device as in claim 6, further comprising a displaceable release button displaceable from an initial state to an actuation state, wherein, with said release button being in said actuation state, said means for releasably retaining said dose-setting mechanism permits said dose-setting mechanism to be released from said first position and to be moved by said biasing means from said first position to said second position.

8. An injector device as in claim 1, further comprising a rotatable release ring disposed in said housing, at least one rib being formed on one of an interior of said housing and said release ring, and at least one channel, shaped to accommodate said rib, being formed on the other of said interior of said housing and said release ring, wherein, with said rib and said channel not being axially aligned, said dose-setting mechanism being retained in said first position, and wherein, said release ring is rotatable relative to said housing to axially align said rib and said channel to permit said dose-setting mechanism to be released from said first position.

9. An injector device as in claim 8, further comprising a displaceable release button, said release button being movable from an initial state to an actuation state, said release button having an angled actuation surface, said release ring including an angled engagement surface, wherein, with said release button moving from said initial state to said actuation state, said actuation surface engages said engagement surface with a torque being generated about said release ring which causes said release ring to rotate relative to said housing.

10. An injector device as in claim 1, wherein said cartridge engagement surface is defined on a leadscrew extending from said dose-setting mechanism.

11. An injector device as in claim 10, further comprising means for preventing rotation of said leadscrew relative to said dose-setting mechanism.

12. An injector device as in claim 10, further comprising means for selectively preventing rotation of said leadscrew relative to said dose-setting mechanism.

13. An injector device as in claim 12, wherein said means for selectively preventing rotation of said leadscrew relative to said dose-setting mechanism includes a retract nut, through which said leadscrew extends, and a radially-inwardly deflectable tab for selectively engaging said retract nut and preventing rotation of said retract nut relative to said dose-setting mechanism.

14. An injector device as in claim 13, further comprising a locking ring mountable onto said dose-setting mechanism, said locking ring causing inward deflection of said tab when mounted onto said dose-setting mechanism, thereby causing said tab to engage said retract nut and prevent rotation of said retract nut relative to said dose-setting mechanism.

15. An injector device as in claim 14, further comprising means for selectively mounting and dismounting said locking ring from said dose-setting mechanism.

16. An injector device as in claim 14, further comprising a stop positioned to maintain said locking ring in a fixed position relative to said housing during a portion of movement of said dose-setting mechanism from said first position to said second position, said locking ring being mounted onto said dose-setting mechanism with said locking ring being maintained in said fixed position and said dose-setting mechanism moving.

17. An injector device as in claim 1, wherein said dose-setting mechanism being adjustable to repeatedly set consecutive doses.

18. An injector device as in claim 17, wherein said consecutive doses are of varying volumes.

19. An injector device as in claim 1, wherein said dose-setting mechanism being adjustable to set doses of varying volumes.

20. An injector device for automatic reconstitution of a substance comprising:
    a dose-setting mechanism having a cartridge engagement surface extending therefrom, said dose-setting mechanism being adjustable to set a dose for the injector device;
    a housing cooperatively engaging said dose-setting mechanism;
    a spring for selectively moving said dose-setting mechanism from a first position to a second position relative to said housing, said cartridge engagement surface moving a predetermined distance relative to said housing with said dose-setting mechanism moving from said first position to said second position; and,
    a rotatable release ring disposed in said housing, at least one rib being formed on one of an interior of said housing and said release ring, and at least one channel, shaped to accommodate said rib, being formed on the other of said interior of said housing and said release ring, wherein, with said rib and said channel not being axially aligned, said dose-setting mechanism being retained in said first position, and wherein, said release ring is rotatable relative to said housing to axially align said rib and said channel to permit said dose-setting mechanism to be released from said first position.

21. An injector device as in claim 20, further comprising a displaceable release button, said release button being movable from an initial state to an actuation state, said release button having an angled actuation surface, said release ring including an angled engagement surface, wherein, with said release button moving from said initial state to said actuation state, said actuation surface engages said engagement surface with a torque being generated about said release ring which causes said release ring to rotate relative to said housing.

22. An injector device for automatic reconstitution of a substance comprising:
    a dose-setting mechanism having a leadscrew extending therefrom with a cartridge engagement surface being defined on said leadscrew, said dose-setting mechanism being adjustable to set a dose for the injector device;
    means for selectively preventing rotation of said leadscrew relative to said dose-setting mechanism having a retract nut, through which said leadscrew extends, and a radially-inwardly deflectable tab for selectively engaging said retract nut and preventing rotation of said retract nut relative to said dose-setting mechanism;
    a housing cooperatively engaging said dose-setting mechanism;

a spring for selectively moving said dose-setting mechanism from a first position to a second position relative to said housing, said cartridge engagement surface moving a predetermined distance relative to said housing with said dose-setting mechanism moving from said first position to said second position; and, a locking ring mountable onto said dose-setting mechanism, said locking ring causing inward deflection of said tab when mounted onto said dose-setting mechanism, thereby causing said tab to engage said retract nut and prevent rotation of said retract nut relative to said dose-setting mechanism.

23. An injector device as in claim 22, further comprising means for selectively mounting and dismounting said locking ring from said dose-setting mechanism.

24. An injector device as in claim 22, further comprising a stop positioned to maintain said locking ring in a fixed position relative to said housing during a portion of movement of said dose-setting mechanism from said first position to said second position, said locking ring being mounted onto said dose-setting mechanism with said locking ring being maintained in said fixed position and said dose-setting mechanism moving.

25. An injector device for automatic reconstitution of a substance comprising:

a dose-setting mechanism having a cartridge engagement surface extending therefrom, said dose-setting mechanism being adjustable to set a dose for the injector device;

a housing cooperatively engaging said dose-setting mechanism;

a spring for selectively moving said dose-setting mechanism from a first position to a second position relative to said housing, said cartridge engagement surface moving a predetermined distance relative to said housing with said dose-setting mechanism moving from said first position to said second position, wherein said dose-setting mechanism being adjustable to repeatedly set consecutive doses.

26. An injector device as in claim 25, wherein said consecutive doses are of varying volumes.

* * * * *